United States Patent
Naidu et al.

(10) Patent No.: US 9,540,393 B2
(45) Date of Patent: Jan. 10, 2017

(54) INHIBITORS OF HUMAN IMMUNODEFICIENCY VIRUS REPLICATION

(71) Applicant: VIIV HEALTHCARE UK (NO.5) LIMITED, Brentford, Middlesex (GB)

(72) Inventors: B. Narasimhulu Naidu, Durham, CT (US); Manoj Patel, Berlin, CT (US); Stanley D'Andrea, Wallingford, CT (US); Zhizhen Barbara Zheng, Cheshire, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 14/773,028

(22) PCT Filed: Mar. 7, 2014

(86) PCT No.: PCT/US2014/021867
§ 371 (c)(1),
(2) Date: Sep. 4, 2015

(87) PCT Pub. No.: WO2014/159076
PCT Pub. Date: Oct. 2, 2014

(65) Prior Publication Data
US 2016/0039844 A1   Feb. 11, 2016

Related U.S. Application Data

(60) Provisional application No. 61/781,315, filed on Mar. 14, 2013.

(51) Int. Cl.
| | | |
|---|---|---|
| A61K 31/535 | (2006.01) | |
| C07D 498/22 | (2006.01) | |
| A61K 31/519 | (2006.01) | |
| A61K 31/5383 | (2006.01) | |
| C07D 487/04 | (2006.01) | |
| C07D 487/16 | (2006.01) | |
| C07D 498/16 | (2006.01) | |
| A61K 45/06 | (2006.01) | |
| A61K 31/529 | (2006.01) | |
| A61K 31/5386 | (2006.01) | |
| C07D 471/22 | (2006.01) | |
| C07D 498/18 | (2006.01) | |

(52) U.S. Cl.
CPC ........... *C07D 498/22* (2013.01); *A61K 31/519* (2013.01); *A61K 31/529* (2013.01); *A61K 31/5383* (2013.01); *A61K 31/5386* (2013.01); *A61K 45/06* (2013.01); *C07D 471/22* (2013.01); *C07D 487/04* (2013.01); *C07D 487/16* (2013.01); *C07D 498/16* (2013.01); *C07D 498/18* (2013.01)

(58) Field of Classification Search
None
See application file for complete search history.

(56) References Cited

U.S. PATENT DOCUMENTS 8,633,200 B2 *   1/2014   Pendri ................... C07D 487/04
                                              514/259.3

FOREIGN PATENT DOCUMENTS

| WO | WO 2007131350 A1 | 11/2007 |
|---|---|---|
| WO | WO 2009062285 A1 | 5/2009 |
| WO | WO 2009062288 A1 | 5/2009 |
| WO | WO 2009062289 A1 | 5/2009 |
| WO | WO 2009062308 A1 | 5/2009 |
| WO | WO 2010130034 A1 | 11/2010 |
| WO | WO 2010130842 A1 | 11/2010 |
| WO | WO 2011015641 A1 | 2/2011 |
| WO | WO 2011076765 A1 | 6/2011 |
| WO | WO 2012003497 A1 | 1/2012 |
| WO | WO 2012003498 A1 | 1/2012 |
| WO | WO 2012033735 A1 | 3/2012 |
| WO | WO 2012065963 A2 | 5/2012 |
| WO | WO 2012066442 A1 | 5/2012 |
| WO | WO 2014028384 A1 | 2/2014 |

OTHER PUBLICATIONS

Palella, et al., "Declining Morbidity and Mortality Among Patients with Advanced Human Immunodeficiency Virus Infection," The New England Journal of Medicine, vol. 338, No. 13, Mar. 26, 1998, pp. 853-860.
Johnson, et al., "Virus Assay (Virus Yield Assay)," Techniques in HIV Research, eds. Anna Aldovini and Bruce D. Walker, New York: Stockton Press 1990, pp. 71-76.

* cited by examiner

*Primary Examiner* — Heidi Reese
(74) *Attorney, Agent, or Firm* — Robert H. Brink; R. Steve Thomas; Edward R. Gimmi

(57) ABSTRACT

The disclosure generally relates to compounds of formula (I), including compositions and methods for treating human immunodeficiency virus (HIV) infection. The disclosure provides novel inhibitors of HIV, pharmaceutical compositions containing such compounds, and methods for using these compounds in the treatment of HIV infection.

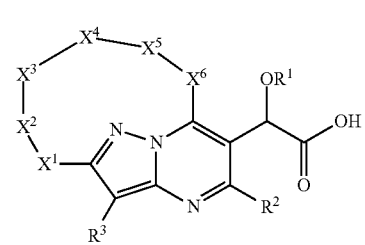

15 Claims, No Drawings

INHIBITORS OF HUMAN IMMUNODEFICIENCY VIRUS REPLICATION

CROSS-REFERENCE TO RELATED APPLICATIONS

This application claims priority to U.S. Provisional Patent Application Ser. No. 61/781,315, filed Mar. 14, 2013, which is incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33.3 million people worldwide are infected with the virus (UNAIDS Report on the Global AIDS Epidemic 2010). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

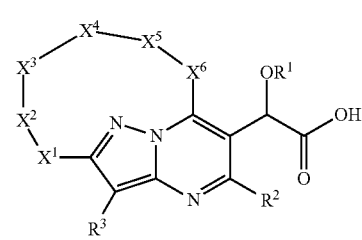

where:
$R^1$ is hydrogen or alkyl;
$R^2$ is hydrogen or alkyl;
$R^3$ is hydrogen, alkyl or halo;
$X^1$ is —CONH—, —CONHCH$_2$CO—, —CONHCH$_2$C(OH)H—, or —NH—;
$X^2$ is absent or benzyl wherein the benzyl can be substituted with 0-3 substituents selected from halo, alkyl, haloalkyl, alkoxy, and haloalkoxy;
$X^3$ is O or absent when $X^2$ is absent;
$X^4$ is alkylene or alkenylene;
$X^5$ is O or absent; and
$X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or $X^6$ is phenyl or oxazinyl and is substituted with 0-3 substituents selected from halo, alkyl, haloalkyl, alkoxy, and haloalkoxy;
or a pharmaceutically acceptable salt thereof.

Another aspect of the invention is a compound of formula I where $R^1$ is hydrogen or alkyl; $R^2$ is hydrogen or alkyl; $R^3$ is hydrogen, alkyl or halo; $X^1$ is —CONH— or —NH—; $X^2$ is absent or benzyl wherein the benzyl can be substituted with 0-3 substituents selected from halo, alkyl, haloalkyl, alkoxy, and haloalkoxy; $X^3$ is O or absent when $X^2$ is absent; $X^4$ is alkylene or alkenylene; $X^5$ is O or absent; $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents; or $X^6$ is phenyl or oxazinyl and is substituted with 0-3 substituents selected from halo, alkyl, haloalkyl, alkoxy, and haloalkoxy; or a pharmaceutically acceptable salt thereof.

Another aspect of the invention is a compound of Formula I where $R^1$ is alkyl; $R^2$ is alkyl; $R^3$ is hydrogen; $X^1$ is —CONH— or —NH—; $X^2$ is absent or benzyl wherein the benzyl can be substituted with 0-3 substituents selected from halo, alkyl, haloalkyl, alkoxy, and haloalkoxy; $X^3$ is O or absent when $X^2$ is absent; $X^4$ is alkylene or alkenylene; $X^5$ is O or absent; $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents; or $X^6$ is phenyl or oxazinyl and is substituted with 0-3 substituents selected from halo, alkyl, haloalkyl, alkoxy, and haloalkoxy; or a pharmaceutically acceptable salt thereof.

Another aspect of the invention is a compound of Formula I where $R^1$ is alkyl; $R^2$ is alkyl; $R^3$ is hydrogen; $X^1$ is —CONH— or —NH—; $X^2$ is absent or benzyl wherein the benzyl can be substituted with 0-1 halo substituents; $X^3$ is O or absent when $X^2$ is absent; $X^4$ is alkylene or alkenylene; $X^5$ is O or absent; $X^6$ is piperidinyl substituted with 0-1 alkyl substituents; or $X^6$ is phenyl or oxazinyl substituted with 0-1 halo substituents; or a pharmaceutically acceptable salt thereof.

Another aspect of the invention is a compound of Formula I where $R^1$ is alkyl, $R^2$ is alkyl, and $R^3$ is hydrogen.

Another aspect of the invention is a compound of Formula I where $X^1$ is —CONH—.

Another aspect of the invention is a compound of Formula I where $X^1$ is —NH—.

Another aspect of the invention is a compound of Formula I where $X^2$ is benzyl substituted with 0-3 substituents selected from halo, alkyl, haloalkyl, alkoxy, and haloalkoxy; and $X^3$ is O or absent.

Another aspect of the invention is a compound of Formula I where $X^2$ and $X^3$ are absent.

Another aspect of the invention is a compound of Formula I where $X^4$ is propylene, propenylene, butylene, butenylene, pentylene, or pentenylene.

Any scope of any variable, including $R^1$, $R^2$, $R^3$, $X^1$, $X^2$, $X^3$, $X^4$, $X^5$, and $X^6$ can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 8 carbons. "Alkenylene" means a straight or branched divalent alkene group composed of 2 to 8 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1.

TABLE 1

| Example | $EC_{50}$ μM |
|---|---|
| 1 | 1.21 |
| 2 | 0.031 |
| 3 | 0.042 |
| 4 | 1.456 |
| 5 | 12.07 |
| 6 | 0.064 |
| 7 | 0.027 |
| 8 | 0.020 |
| 9 | 0.023 |
| 10 | 0.005 |
| 11 | 0.193 |
| 12 | 0.168 |
| 13 | 0.023 |
| 14 | 0.029 |
| 15 | 0.035 |
| 16 | 0.035 |
| 17 | 0.065 |
| 18 | 0.038 |
| 19 | 1.075 |
| 20 | 0.370 |
| 21 | 0.136 |
| 22 | 0.057 |
| 23 | 0.051 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions known in the art. Intermediates I-3 can be prepared by procedure known in the art or as set forth in the examples below using compound I-1 and compound I-2. Intermediates I-3 can be transformed to intermediates I-5 via intermediates I-4 using conditions known to those skilled in the art. Intermediates I-5 can be oxidized to intermediates I-6 by reactions known in the art, including Davis oxidation. Intermediates I-6 can be oxidized to intermediates I-7 by known conditions, including Dess-Martin oxidation. Intermediates I-7 can be reduced to chiral intermediates I-8 using known conditions in the presence of catalytic chiral ligands. Intermediates I-8 can be converted to the intermediates I-9 by known conditions, including tertiary-butyl acetate and perchloric acid. Sequential coupling of aryl groups to Intermediates I-9 using conditions known in the art, including Suzuki coupling, can provide intermediates 10 and 11. Boronate or boronic acid coupling reagents are commercially available or are prepared by reactions known in the art (for example, PCT Appln. WO20090662285). Intermediates I-11 can be converted to intermediates I-12 by conditions known in the art, including ring closing metathesis. Hydrolysis of intermediates I-12 would provide products I-13 which could be converted to I-14 using conditions known in the art.

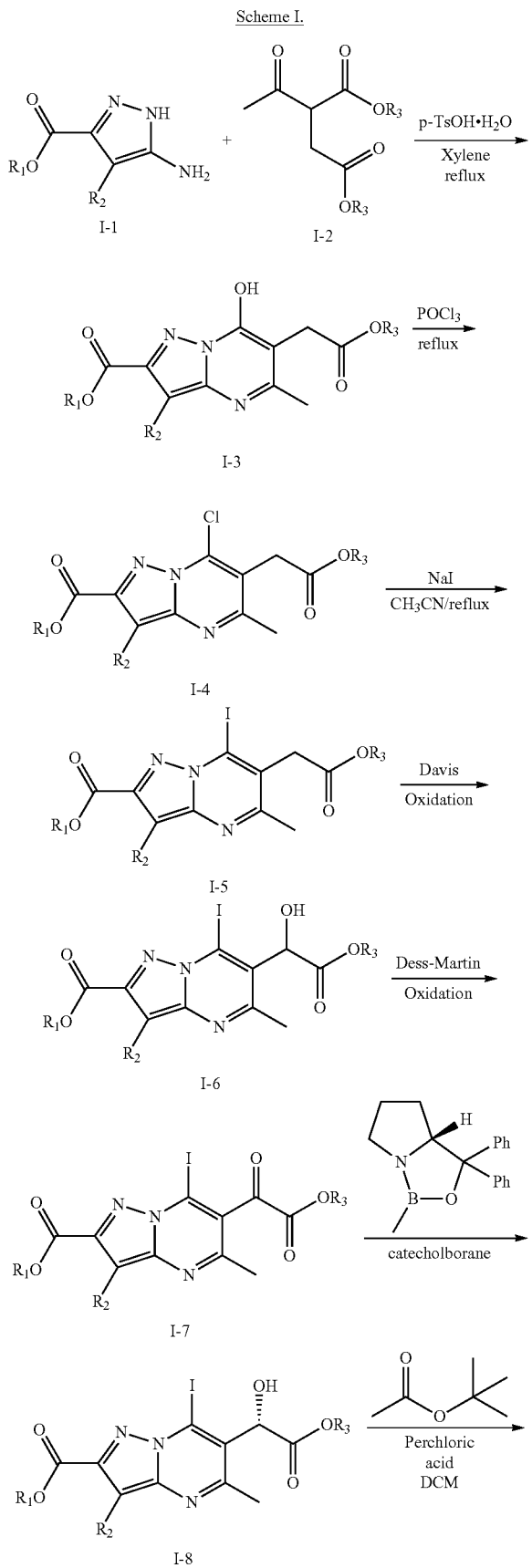

Scheme I.

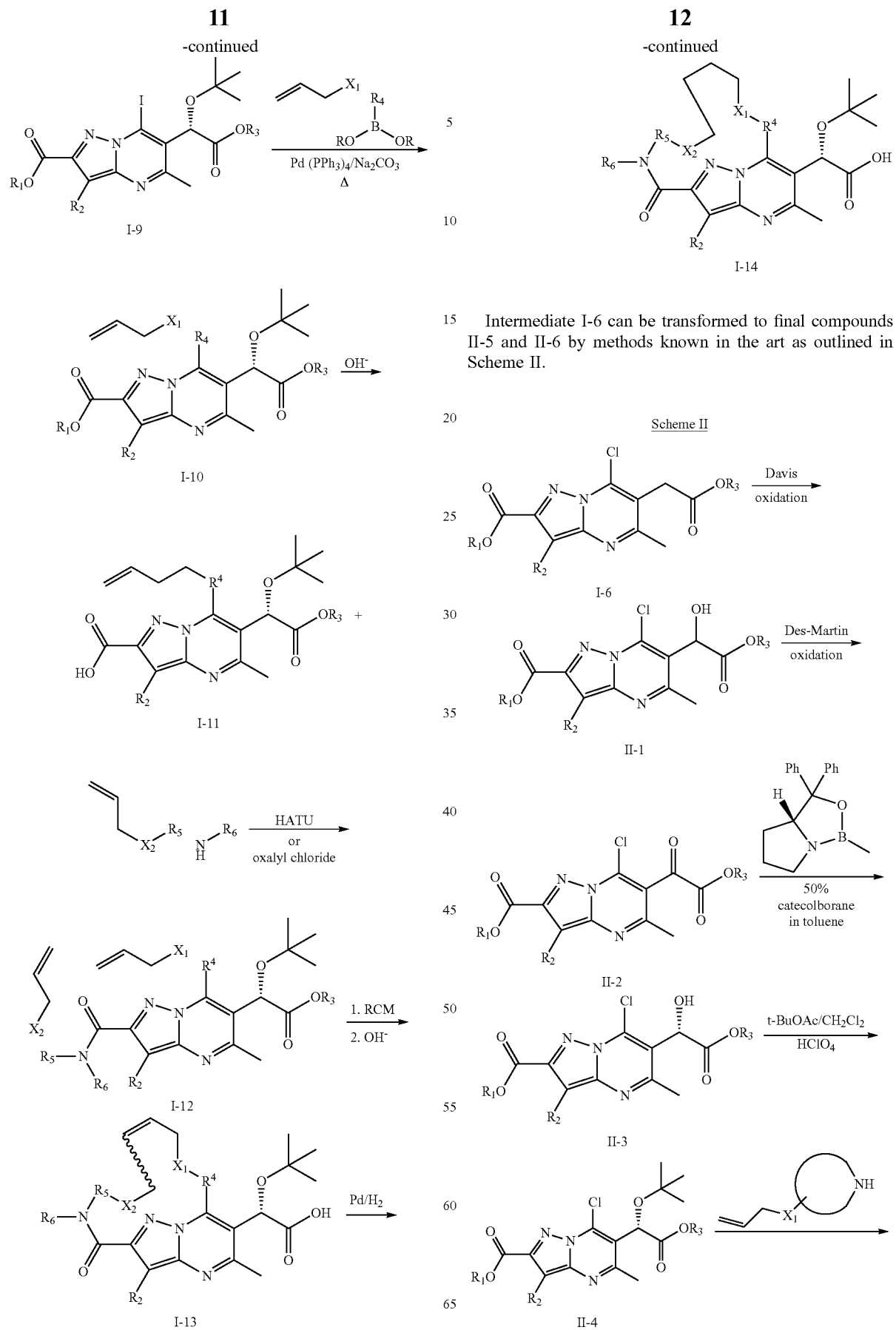
Intermediate I-6 can be transformed to final compounds II-5 and II-6 by methods known in the art as outlined in Scheme II.

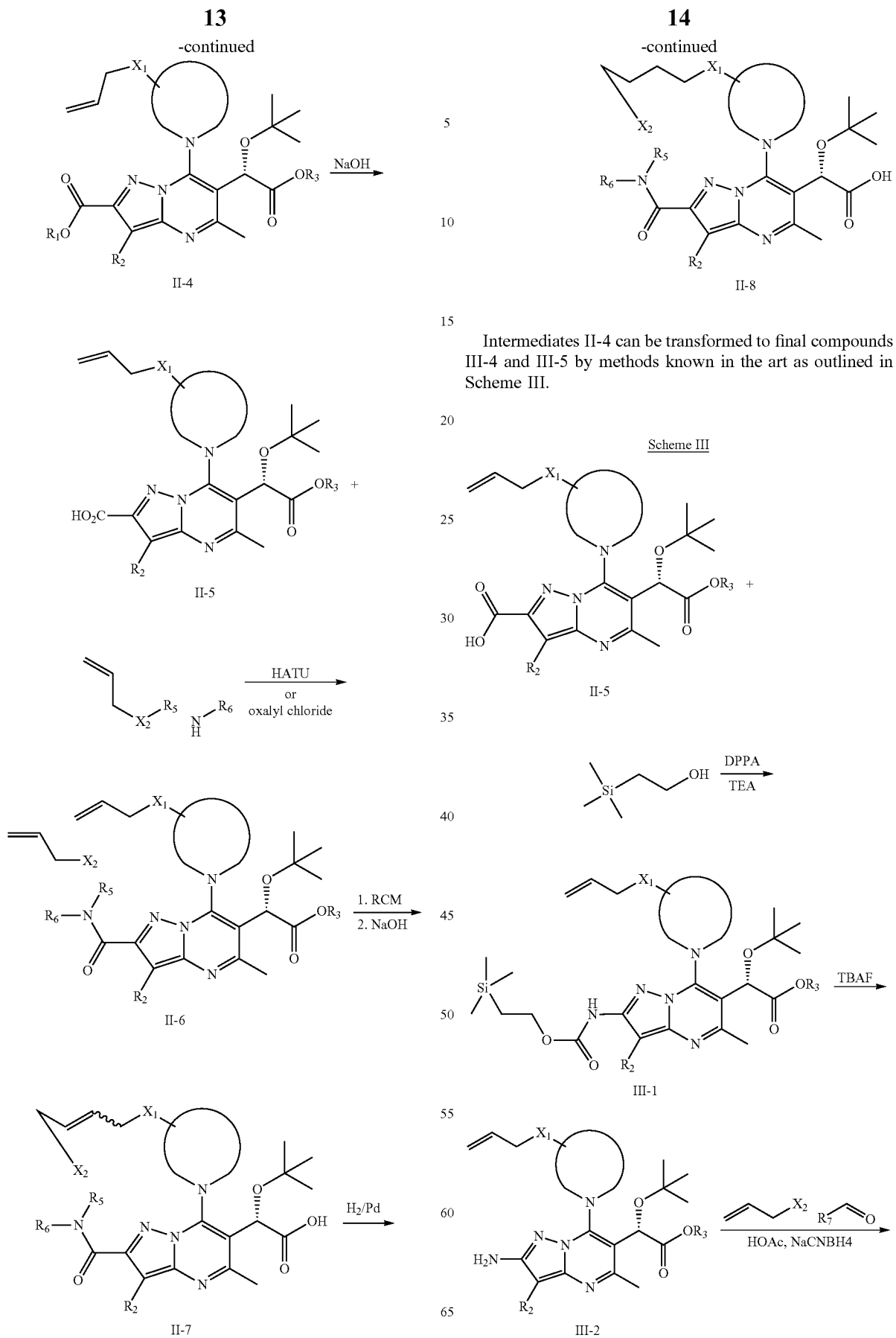
Intermediates II-4 can be transformed to final compounds III-4 and III-5 by methods known in the art as outlined in Scheme III.

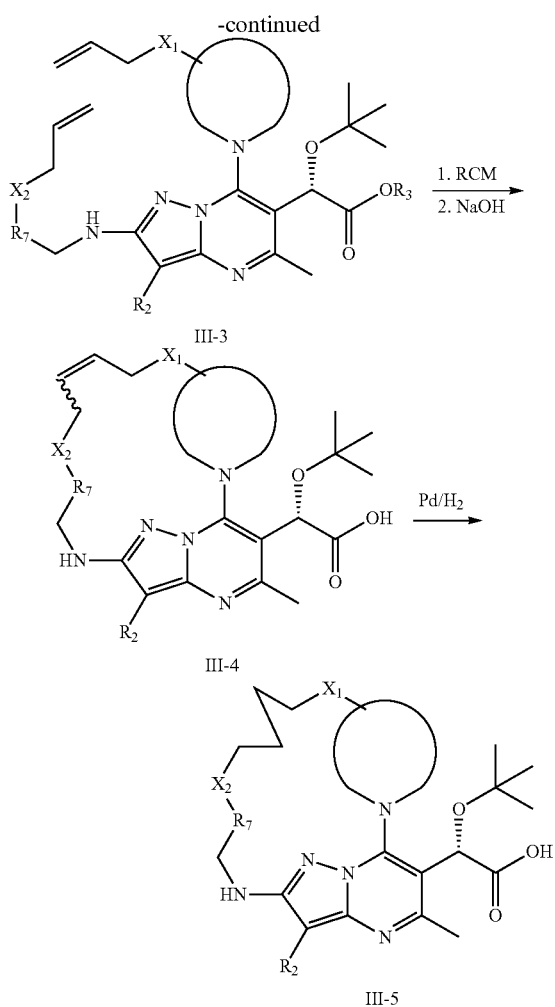

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H₂O/acetonitrile with 10 mM NH₄OAc and mobile phase B:A: 9:1 acetonitrile/H₂O with: 10 mM NH₄OAc or mobile phase A: 95:5 H₂O/MeOH with 20 mM NH₄OAc and mobile phase B: 95:5 MeOH/H₂O with 20 mM NH₄OAc.

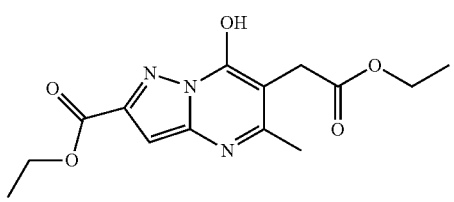 [SMILES: CCOC(=O)Cc1c(C)nc2cc(C(=O)OCC)nn2c1O]

Ethyl 6-(2-ethoxy-2-oxoethyl)-7-hydroxy-5-methyl-pyrazolo[1,5-a]pyrimidine-2-carboxylate A suspension of ethyl 5-amino-1H-pyrazole-3-carboxylate (35.5 g, 229 mmol, prepared according to WO 2008015271), diethyl 2-acetylsuccinate (51.2 mL, 275 mmol) and TsOH.H₂O (0.218 g, 1.144 mmol) in o-xylene (500 mL) was refluxed using a Dean-Stork condensor for 5 h. (Note: The suspension turned into a clear homogeneous solution and then in about 15 min a yellow solid started precipitated out of solution). Then, the reaction mixture was cooled, diluted with hexanes (250 mL), filtered, washed with hexanes and dried to afford ethyl 6-(2-ethoxy-2-oxoethyl)-7-hydroxy-5-methylpyrazolo[1,5-a]pyrimidine-2-carboxylate (53 g, 75% yield) as light yellow solid. ¹H NMR (500 MHz, DMSO-d₆) δ 12.61 (br. s., 1H), 6.49 (s, 1H), 4.34 (q, J=7.1 Hz, 2H), 4.09 (q, J=7.1 Hz, 2H), 3.57 (s, 2H), 2.34 (s, 3H), 1.33 (t, J=7.2 Hz, 3H), 1.19 (t, J=7.0 Hz, 3H). LCMS (M+1)=308.04.

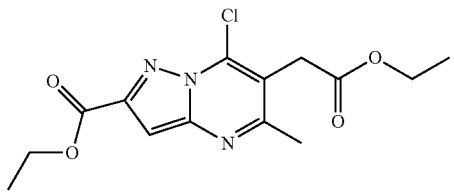

Ethyl 7-chloro-6-(2-ethoxy-2-oxoethyl)-5-methyl-pyrazolo[1,5-a]pyrimidine-2-carboxylate A mixture of ethyl 6-(2-ethoxy-2-oxoethyl)-7-hydroxy-5-methylpyrazolo[1,5-a]pyrimidine-2-carboxylate (25 g, 81 mmol), and N,N-dimethylaniline (20.6 mL, 163 mmol) in POCl₃ (100 mL) was heated at 120° C. for 3 h. Then the reaction was cooled to rt and concentrated in vacuo to half the volume. It was poured into a large quantity of ice water and stirred for 20 min. Precipitates formed and were collected by filtration. This solid was dissolved in ethyl acetate (1 L) and washed with water. The aqueous phase was back-extracted with ethyl acetate and the combined organic layers were washed with brine (200 mL), dried (Na₂SO₄), filtered and concentrated in vacuo. The crude was then triturated with EtOAc/hexane to afford ethyl 7-chloro-6-(2-ethoxy-2-oxoethyl)-5-methylpyrazolo[1,5-a]pyrimidine-2-carboxylate (22 g, 67.5 mmol, 83% yield) as light yellow solid. ¹H NMR (500 MHz, CDCl₃) δ 7.21 (s, 1H), 4.52 (q, J=7.2 Hz, 2H), 4.24 (q, J=7.2 Hz, 2H), 3.94 (s, 2H), 2.66 (s, 3H), 1.48 (t, J=7.0 Hz, 3H), 1.30 (t, J=7.2 Hz, 3H). LCMS (M+1)=326.2.

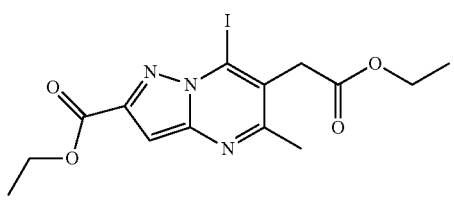 [SMILES: CCOC(=O)Cc1c(C)nc2cc(C(=O)OCC)nn2c1I]

Ethyl 6-(2-ethoxy-2-oxoethyl)-7-iodo-5-methylpyrazolo[1,5-a]pyrimidine-2-carboxylate Ethyl 7-chloro-6-(2-ethoxy-2-oxoethyl)-5-methylpyrazolo[1,5-a]pyrimidine-2-carboxylate (5 g, 15.35 mmol) and sodium iodide (9.20 g, 61.4 mmol) were suspended in acetonitrile (80 mL) and the resulting mixture was heated at 80° C. for 2 h. At this point LCMS indicated completion of reaction and appearance of the desired product. After cooling to rt, the reaction mixture was diluted with ethyl acetate and washed with water and aqueous Na₂S₂O₃, dried (Na₂SO₄), filtered and concentrated. Then crude product was triturated with ethyl acetate/hexane to afford ethyl 6-(2-ethoxy-2-oxoethyl)-7-iodo-5-methylpyrazolo[1,5-a]pyrimidine-2-carboxylate (5.7 g, 13.66 mmol, 89% yield) as off white solid. ¹H NMR (500 MHz, CDCl₃) δ: 7.32 (s, 1H), 4.51 (d, J=7.0 Hz, 2H), 4.25 (d, J=7.0 Hz, 2H), 4.02 (s, 2H), 2.68 (s, 3H), 1.48 (t, J=7.2 Hz, 3H), 1.31 (t, J=7.2 Hz, 3H). LCMS (M+H)=418.2.

(100 mL), dried (Na₂SO₄), filtered, concentrated and the residue was purified by silica gel chromatography (5-70% EtOAc/hexane) to afford desired ethyl 6-(2-ethoxy-2-oxoacetyl)-7-iodo-5-methylpyrazolo[1,5-a]pyrimidine-2-carboxylate (2.5 g, 5.80 mmol, 91% yield) as off-white solid. ¹H NMR (400 MHz, CDCl₃) δ: 7.36 (s, 1H), 4.50 (dq, J=14.5, 7.1 Hz, 4H), 2.56 (s, 3H), 1.46 (t, J=7.2 Hz, 3H), 1.48 (t, J=7.2 Hz, 3H). LCMS (M+H)=431.87.

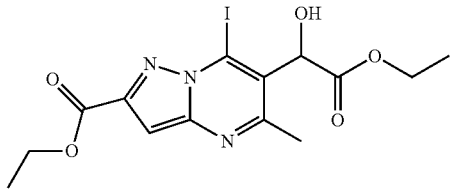 [SMILES: CCOC(=O)c1cc2nc(C)c(C(O)C(=O)OCC)c(I)n2n1]

Ethyl 6-(2-ethoxy-1-hydroxy-2-oxoethyl)-7-iodo-5-methylpyrazolo[1,5-a]pyrimidine-2-carboxylate To a stirred solution of 0.9M KHMDS/THF (39.1 mL, 35.2 mmol) in THF (100 mL) at −78° C. was added a THF (50 mL) solution of ethyl 6-(2-ethoxy-2-oxoethyl)-7-iodo-5-methylpyrazolo[1,5-a]pyrimidine-2-carboxylate (11.3 g, 27.1 mmol) over 5 min. After 30 min, a THF (50 mL) solution of 3-phenyl-2-(phenylsulfonyl)-1,2-oxaziridine (9.20 g, 35.2 mmol) was added to the red reaction mixture and stirred for additional 30 min at −78° C. Then, the resulting orange reaction mixture was quenched with sat. NH₄Cl (50 mL), diluted with EtOAc (200 mL), washed with water (100 mL), brine (100 mL), dried (Na₂SO₄), filtered and concentrated to give solid. This solid was triturated with small amount of ethyl acetate and solids were filtered, washed with hexanes and dried under high vac to afford ethyl 6-(2-ethoxy-1-hydroxy-2-oxoethyl)-7-iodo-5-methylpyrazolo[1,5-a]pyrimidine-2-carboxylate (7.3 g, 16.85 mmol, 62.2% yield) as light yellow solid. ¹H NMR (500 MHz, CDCl₃) δ: 7.33 (s, 1H), 5.75 (d, J=2.1 Hz, 1H), 4.52 (qd, J=7.1, 1.2 Hz, 2H), 4.37-4.30 (m, 2H), 3.57 (d, J=2.4 Hz, 1H), 2.63 (s, 3H), 1.48 (t, J=7.2 Hz, 3H), 1.27 (t, J=7.0 Hz, 3H). LCMS (M+H)=434.1.

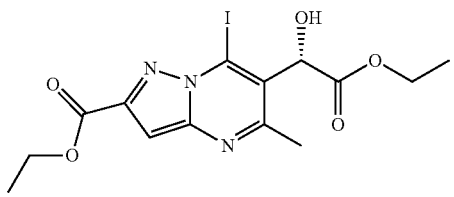

(S)-Ethyl 6-(2-ethoxy-1-hydroxy-2-oxoethyl)-7-iodo-5-methylpyrazolo[1,5-a]pyrimidine-2-carboxylate To a stirred yellow solution of ethyl 6-(2-ethoxy-2-oxoacetyl)-7-iodo-5-methylpyrazolo[1,5-a]pyrimidine-2-carboxylate (6.4 g, 14.84 mmol) in anhydrous toluene (300 mL) was added 1.1M (R)-1-methyl-3,3-diphenylhexahydropyrrolo[1,2-c][1,3,2]oxazaborole/toluene (5.40 mL, 5.94 mmol). The mixture was cooled to −35° C. and a solution of 50% catecholborane/toluene (5.09 mL, 20.78 mmol) was added over 10 min. After 30 min, the reaction mixture was slowly warmed to −15° C. and stirred for additional 2 h, then diluted with EtOAc (600 mL) and sat. Na₂CO₃ (100 mL). The mixture was stirred vigorously for 30 min, and the organic phase washed with sat Na₂CO₃ (2×100 mL), dried (Na₂SO₄), filtered, concentrated and the residue was purified by silica gel chromatography (5-100% EtOAc/hexane) to afford desired (S)-ethyl 6-(2-ethoxy-1-hydroxy-2-oxoethyl)-7-iodo-5-methylpyrazolo[1,5-a]pyrimidine-2-carboxylate (5.3 g, 12.23 mmol, 82% yield) as off-white solid. ¹H NMR (500 MHz, CDCl₃) δ: 7.33 (s, 1H), 5.75 (d, J=2.4 Hz, 1H), 4.52 (qd, J=7.1, 1.1 Hz, 2H), 4.38-4.29 (m, 2H), 3.59 (d, J=2.4 Hz, 1H), 2.63 (s, 3H), 1.48 (t, J=7.2 Hz, 3H), 1.27 (t, J=7.2 Hz, 3H). LCMS (M+H)=434.2.

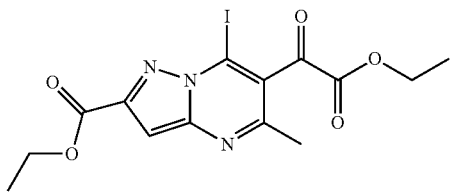 [SMILES: CCOC(=O)C(=O)c1c(C)nc2cc(C(=O)OCC)nn2c1I]

Ethyl 6-(2-ethoxy-2-oxoacetyl)-7-iodo-5-methylpyrazolo[1,5-a]pyrimidine-2-carboxylate To a mixture of ethyl 6-(2-ethoxy-1-hydroxy-2-oxoethyl)-7-iodo-5-methylpyrazolo[1,5-a]pyrimidine-2-carboxylate (3.7 g, 6.41 mmol) in CH₂Cl₂ (80 mL) was added Dess-Martin Periodinane (2.72 g, 6.41 mmol) and the resulting mixture was stirred at rt for 1 hr. Then diluted with ethyl acetate (500 mL) and washed with sat. NaHCO₃ solution

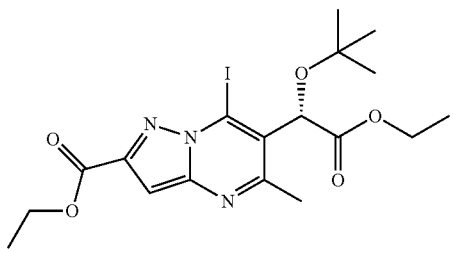 [SMILES: CCOC(=O)c1cc2nc(C)c([C@H](OC(C)(C)C)C(=O)OCC)c(I)n2n1]

(S)-Ethyl 6-(1-(tert-butoxy)-2-ethoxy-2-oxoethyl)-7-iodo-5-methylpyrazolo[1,5-a]pyrimidine-2-carboxylate To a stirred solution of (S)-ethyl 6-(2-ethoxy-1-hydroxy-2-oxoethyl)-7-iodo-5-methylpyrazolo[1,5-a]pyrimidine-2-carboxylate (5.3 g, 12.23 mmol) in CH₂Cl₂ (150 mL) and t-butyl acetate (105 mL) was added perchloric acid (3.15 mL, 36.7 mmol) at rt and sealed the reaction flask. After 3 h, the reaction mixture was diluted with $CH_2Cl_2$ (100 mL), carefully quenched with sat. $NaHCO_3$ (50 mL), organic layer separated and washed with brine (100 mL), dried ($Na_2SO_4$), filtered and concentrated to give yellow liquid. This was purified by flash column chromatography on silica gel column using (10-50% EtOAc/Hex as eluant) to afford the desired (S)-ethyl 6-(1-(tert-butoxy)-2-ethoxy-2-oxoethyl)-7-iodo-5-methylpyrazolo[1,5-a]pyrimidine-2-carboxylate (4.5 g, 8.28 mmol, 67.7% yield) as viscous oil. 700 mg of starting material was also recovered. $^1H$ NMR (500 MHz, $CDCl_3$) δ: 7.31 (s, 1H), 5.56 (s, 1H), 4.51 (q, J=7.1 Hz, 2H), 4.26-4.16 (m, 2H), 2.71 (s, 3H), 1.48 (t, J=7.2 Hz, 3H), 1.30 (s, 9H), 1.23 (t, J=7.0 Hz, 3H). LCMS (M+H)=490.0.

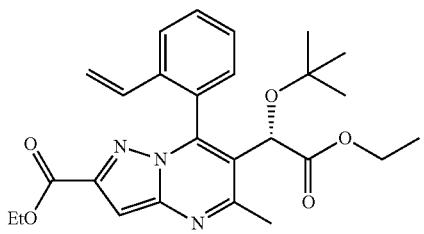

Ethyl 6-((S)-1-(tert-butoxy)-2-ethoxy-2-oxoethyl)-5-methyl-7-(2-vinylphenyl)pyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (300 mg, 0.613 mmol), (2-vinylphenyl)boronic acid (109 mg, 0.736 mmol) and 2N $Na_2CO_3$ (0.613 mL, 1.226 mmol) in DMF (5 mL) was degassed for 30 min. tetrakis(triphenylphosphine)palladium(0) (49.6 mg, 0.043 mmol) was then added and the degassing was continue for another 15 min. The mixture was then heated at 100° C. for 16 h. At this point LCMS indicates completion of reaction and appearance of desired product. After cooling to room temp, water was added (20 mL) and the mixture was extracted with ether (2×50 mL), washed with brine (25 mL), dried ($Na_2SO_4$), filtered and concentrated. The crude was then purified by silica gel chromatography (5-60% EtOAc/hexane) to afford ethyl 6-((S)-1-(tert-butoxy)-2-ethoxy-2-oxoethyl)-5-methyl-7-(2-vinylphenyl)pyrazolo[1,5-a]pyrimidine-2-carboxylate (110 mg, 0.236 mmol, 38.5% yield) as mixture of atrope isomers (approx 10% of minor atrope isomer was present). $^1H$ NMR (400 MHz, $CDCl_3$) δ 7.84 (d, J=8.0 Hz, 1H), 7.62-7.56 (m, 1H), 7.49-7.43 (m, 1H), 7.32 (dd, J=7.7, 0.9 Hz, 1H), 7.13-7.08 (m, 1H), 6.26 (dd, J=17.4, 10.9 Hz, 1H), 5.74 (dd, J=17.3, 0.8 Hz, 1H), 5.14-5.07 (m, 1H), 4.88 (s, 1H), 4.42-4.35 (m, 2H), 4.12 (q, J=7.0 Hz, 2H), 2.79 (s, 3H), 1.41-1.35 (m, 3H), 1.23-1.17 (m, 3H), 1.09 (s, 9H). LCMS (M+H)=466.35.

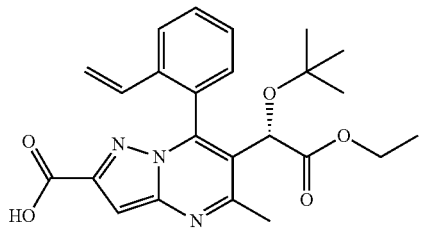 [SMILES: C=Cc1ccccc1-c1c([C@H](OC(C)(C)C)C(=O)OCC)c(C)nc2cc(C(=O)O)nn12]

6-((S)-1-(tert-Butoxy)-2-ethoxy-2-oxoethyl)-5-methyl-7-(2-vinylphenyl)pyrazolo[1,5-a]pyrimidine-2-carboxylic acid To a solution of ethyl 6-((S)-1-(tert-butoxy)-2-ethoxy-2-oxoethyl)-5-methyl-7-(2-vinylphenyl)pyrazolo[1,5-a]pyrimidine-2-carboxylate (101 mg, 0.217 mmol) in THF (3 mL) was added 1N NaOH (0.217 mL, 0.217 mmol) and the mixture was stirred at room temp for 16 h. Water (3 mL) was then added and the mixture was acidified with 1N HCl, extracted with ether (2×25 mL), washed with brine (25 mL), dried ($Na_2SO_4$), filtered and concentrated to afford 6-((S)-1-(tert-butoxy)-2-ethoxy-2-oxoethyl)-5-methyl-7-(2-vinylphenyl)pyrazolo[1,5-a]pyrimidine-2-carboxylic acid (80 mg, 0.183 mmol, 84% yield) as light yellow solid. $^1H$ NMR (400 MHz, $CDCl_3$) δ 7.86 (d, J=8.1 Hz, 1H), 7.65-7.59 (m, 1H), 7.52-7.45 (m, 1H), 7.31-7.29 (m, 1H), 7.22 (s, 1H), 6.24 (dd, J=17.4, 11.0 Hz, 1H), 5.82-5.73 (m, 1H), 5.17-5.10 (m, 1H), 4.92 (s, 1H), 4.18-4.09 (m, 2H), 2.82 (s, 3H), 1.22-1.18 (m, 3H), 1.11 (s, 9H). LCMS (M+H)=438.4.

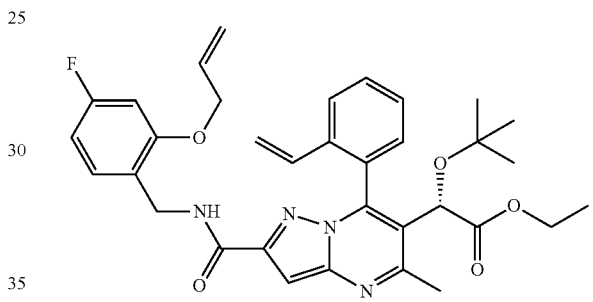

(2S)-Ethyl 2-(2-((2-(allyloxy)-4-fluorobenzyl)carbamoyl)-5-methyl-7-(2-vinylphenyl)pyrazolo[1,5-a]pyrimidin-6-yl)-2-(tert-butoxy)acetate To a mixture of 6-((S)-1-(tert-butoxy)-2-ethoxy-2-oxoethyl)-5-methyl-7-(2-vinylphenyl)pyrazolo[1,5-a]pyrimidine-2-carboxylic acid (50 mg, 0.114 mmol) and (2-(allyloxy)-4-fluorophenyl)methanamine, HCl (49.8 mg, 0.229 mmol) in DMF (1.5 mL) was added DIEA (0.100 mL, 0.571 mmol), HATU (87 mg, 0.229 mmol) and DMAP (2.79 mg, 0.023 mmol) and the resulting mixture was stirred at room temp for 16 h. At this point LCMS indicates completion of reaction. Water was then added and the mixture was extracted with ethyl acetate (2×25 mL), washed with brine (25 mL), dried ($Na_2SO_4$), filtered and concentrated. Crude was then purified by biotage (10-70% EtOAc/hexane) to afford (2S)-ethyl 2-(2-((2-(allyloxy)-4-fluorobenzyl)carbamoyl)-5-methyl-7-(2-vinylphenyl)pyrazolo[1,5-a]pyrimidin-6-yl)-2-(tert-butoxy)acetate (37 mg, 0.062 mmol, 53.9% yield) as off-white solid. $^1H$ NMR (400 MHz, $CDCl_3$) δ 7.84 (d, J=8.0 Hz, 1H), 7.59 (t, J=7.7 Hz, 1H), 7.50-7.45 (m, 1H), 7.37-7.31 (m, 1H), 7.27-7.22 (m, 1H), 6.61-6.51 (m, 2H), 6.25 (dd, J=17.3, 11.0 Hz, 1H), 5.86 (ddt, J=17.3, 10.5, 5.2 Hz, 1H), 5.78-5.69 (m, 1H), 5.37-5.31 (m, 1H), 5.27-5.19 (m, 1H), 5.15-5.10 (m, 1H), 4.87 (s, 1H), 4.53 (d, J=6.3 Hz, 2H), 4.43 (dt, J=5.3, 1.5 Hz, 2H), 4.15-4.08 (m, 2H), 2.79 (s, 3H), 1.19 (t, J=7.0 Hz, 3H), 1.10 (s, 9H). LCMS (M+H)=601.6.

Example 1

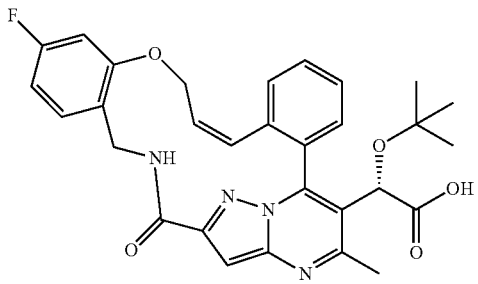 [SMILES: Cc1nc2cc3nn2c(c1[C@H](OC(C)(C)C)C(=O)O)-c1ccccc1/C=C\COc1cc(F)ccc1CNC3=O]

(2S)-2-(tert-Butoxy)-2-[(12Z)-18-fluoro-3-methyl-24-oxo-15-oxa-2,23,26,27-tetraazapentacyclo[23.2.1.0$^{5,27}$.0$^{6,11}$.0$^{16,21}$]octacosa-1(28),2,4,6,8,10,12,16(21),17,19,25-undecaen-4-yl]acetic acid A mixture of (2S)-ethyl 2-(2-((2-(allyloxy)-4-fluorobenzyl)carbamoyl)-5-methyl-7-(2-vinylphenyl)pyrazolo[1,5-a]pyrimidin-6-yl)-2-(tert-butoxy)acetate (22 mg, 0.037 mmol) and Hoveyda-GrubbsII (3.11 mg, 3.66 µmol) catalyst in DCE (1 mL) was heated to reflux for 16 h. After cooling to room temp, mixture was filtered and purified by prep HPLC to afford ester as a mixture of cis and trans isomers. Ester was then treated with 1N NaOH (0.110 mL, 0.110 mmol) in MeOH (1.0 mL) at 60° C. for 3 h. Mixture was then purified by prep HPLC to afford 3 compounds with same MW as desired. Major compound determined to be cis by NMR was isolated (1.1 mg, 5%). $^1$H NMR (500 MHz, CDCl$_3$) δ 8.10 (br. s., 1H), 7.64 (t, J=7.6 Hz, 1H), 7.56-7.48 (m, 1H), 7.36 (t, J=7.8 Hz, 2H), 7.19 (t, J=7.4 Hz, 1H), 7.10 (s, 1H), 6.78 (s, 1H), 6.68-6.61 (m, 1H), 6.48 (d, J=11.8 Hz, 1H), 5.94-5.81 (m, 1H), 5.18 (s, 1H), 5.09 (t, J=11.1 Hz, 1H), 4.89 (d, J=8.5 Hz, 1H), 4.56 (dd, J=14.6, 4.5 Hz, 1H), 4.42 (dd, J=14.5, 6.3 Hz, 1H), 2.86 (s, 3H), 1.22 (s, 9H). LCMS (M+H)=545.5.

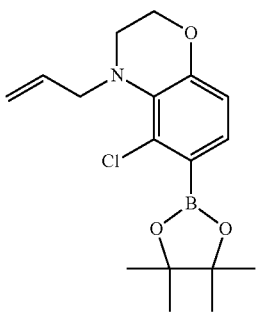 [SMILES: C=CCN1CCOc2ccc(B3OC(C)(C)C(C)(C)O3)c(Cl)c21]

4-Allyl-5-chloro-6-(4,4,5,5-tetramethyl-1,3,2-dioxaborolan-2-yl)-3,4-dihydro-2H-benzo[b][1,4]oxazine To a solution of 5-chloro-6-(4,4,5,5-tetramethyl-1,3,2-dioxaborolan-2-yl)-3,4-dihydro-2H-benzo[b][1,4]oxazine (2.0 g, 6.77 mmol, ref WO 2009/062285) in DMF (50 mL) was added NaH (812 mg, 20.30 mmol) and the resulting mixture was stirred at room temp for 10 min. 3-bromoprop-1-ene (1.717 mL, 20.30 mmol) was then added and the resulting mixture was stirred at room temp for 24 h. Water was then added and the mixture was extracted with ethyl acetate (2×25 mL), washed with water (25 mL), brine (25 mL), dried (Na$_2$SO$_4$), filtered and concentrated. Crude was then purified by biotage using 10-50% EtOAc/hexane to afford 4-allyl-5-chloro-6-(4,4,5,5-tetramethyl-1,3,2-dioxaborolan-2-yl)-3,4-dihydro-2H-benzo[b][1,4]oxazine (1.7 g, 5.07 mmol, 74.9% yield) as viscous oil. $^1$H NMR (500 MHz, CDCl$_3$) δ 7.31 (d, J=8.4 Hz, 1H), 6.81 (d, J=8.4 Hz, 1H), 6.16-5.99 (m, 1H), 5.38-5.28 (m, 1H), 5.25 (d, J=10.1 Hz, 1H), 4.16 (t, J=4.4 Hz, 2H), 3.59 (d, J=6.0 Hz, 2H), 3.11 (t, J=4.4 Hz, 2H), 1.38 (s, 12H). LCMS (M+H)=336.4.

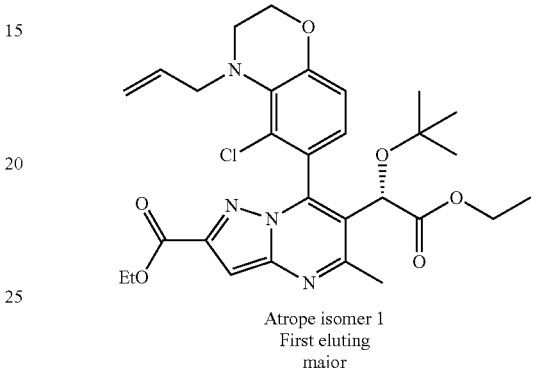

Atrope isomer 1
First eluting
major

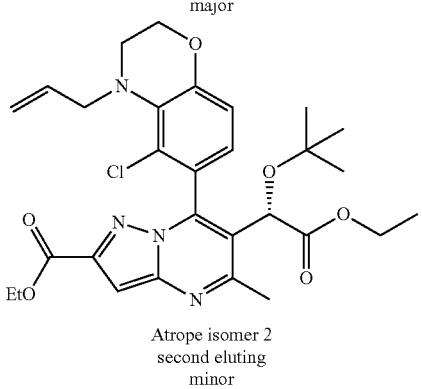

Atrope isomer 2
second eluting
minor

Ethyl 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (150 mg, 0.307 mmol), 4-allyl-5-chloro-6-(4,4,5,5-tetramethyl-1,3,2-dioxaborolan-2-yl)-3,4-dihydro-2H-benzo[b][1,4]oxazine (113 mg, 0.337 mmol) and 2N Na$_2$CO$_3$ (0.307 mL, 0.613 mmol) in DMF (5 mL) was degassed for 15 min.

Tetrakis(triphenylphosphine)palladium(0) (24.80 mg, 0.021 mmol) was then added and the degassing was continue for another 5 min. The mixture was then heated at 100° C. for 16 h. At this point LCMS indicates completion of reaction and appearance of desired product. After cooling to room temp, water was added (50 mL) and the mixture was extracted with ether (2×200 mL), washed with brine (100 mL), dried (Na$_2$SO$_4$), filtered and concentrated. The crude was then purified by prep HPLC to afford two atrope isomers.

Atrope isomer 1, major, first eluting ethyl 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylate (55 mg, 0.096 mmol, 31.4% yield). $^1$H NMR (500 MHz, CDCl$_3$) δ 7.10 (s, 1H), 7.03-6.91 (m, 2H), 6.09-5.96 (m, 1H), 5.35 (d, J=17.2 Hz, 1H), 5.25 (d, J=10.1 Hz, 1H), 5.02 (s, 1H), 4.46-4.34 (m, 2H), 4.26 (t, J=4.2 Hz, 2H), 4.19-4.03 (m, 2H), 3.73 (dd, J=15.4, 5.6 Hz, 1H), 3.60 (dd, J=15.3, 5.8 Hz, 1H), 3.26-3.10 (m, 2H), 2.87 (s, 3H), 1.39 (t, J=7.1 Hz, 3H), 1.20 (t, J=7.2 Hz, 3H), 1.16 (s, 9H). LCMS (M+H)=571.5.

Atrope isomer 2, minor, second eluting ethyl 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylate (25 mg, 0.044 mmol, 14.28% yield). $^1$H NMR (500 MHz, CDCl$_3$) δ 7.22 (d, J=8.5 Hz, 1H), 7.11 (s, 1H), 6.99 (d, J=8.4 Hz, 1H), 6.10-5.96 (m, 1H), 5.34 (d, J=17.0 Hz, 1H), 5.26 (d, J=10.1 Hz, 1H), 5.13 (s, 1H), 4.49-4.33 (m, 2H), 4.31-4.20 (m, 4H), 3.77 (dd, J=15.1, 5.2 Hz, 1H), 3.53 (dd, J=15.1, 6.6 Hz, 1H), 3.29-3.21 (m, 1H), 3.20-3.10 (m, 1H), 2.74 (s, 3H), 1.39 (t, J=7.1 Hz, 3H), 1.30 (t, J=7.1 Hz, 3H), 1.06 (s, 9H). LCMS (M+H)=571.5.

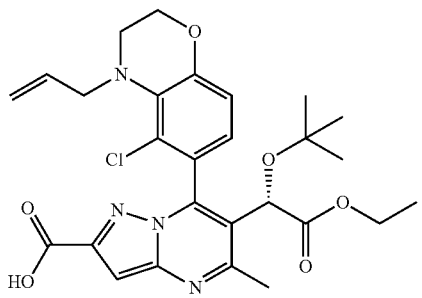 [SMILES: C=CCN1CCOc2ccc(-c3c([C@H](OC(C)(C)C)C(=O)OCC)c(C)nc4cc(C(=O)O)nn34)c(Cl)c21]

7-(4-Allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylic acid (major atrope isomer)

To a solution of ethyl 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylate (70 mg, 0.123 mmol, major atrope isomer) in EtOH (2 mL) was added 1N NaOH (0.123 mL, 0.123 mmol) and the resulting mixture was stirred at room temp for 4 h. At this point LCMS indicates completion of reaction. Solvents were then removed under reduced pressure and the mixture was diluted with water (3 mL), acidified with 1N HCl, extracted with ether (25 mL), washed with brine (10 mL), dried (Na$_2$SO$_4$), filtered and concentrated to afford 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylic acid (50 mg, 0.092 mmol, 75% yield) as off-white solid. $^1$H NMR (500 MHz, CDCl$_3$) δ 7.21 (s, 1H), 7.01 (d, J=8.4 Hz, 1H), 6.91 (d, J=8.5 Hz, 1H), 6.08-5.90 (m, 1H), 5.40-5.34 (m, 1H), 5.27 (d, J=9.6 Hz, 1H), 5.02 (s, 1H), 4.31-4.23 (m, 2H), 4.19-4.06 (m, 2H), 3.72-3.60 (m, 2H), 3.23-3.17 (m, 2H), 2.88 (s, 3H), 1.21-1.18 (m, 3H), 1.17 (s, 9H). LCMS (M+H)=543.5.

7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylic acid (minor atrope isomer)

Similarly to above procedure minor atropisomer was hydrolyzed to afford 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylic acid (100 mg, 0.184 mmol, 84% yield) as off-white solid. $^1$H NMR (500 MHz, CDCl$_3$) δ 7.21 (s, 1H), 7.19 (d, J=8.5 Hz, 1H), 7.05-6.97 (m, 1H), 6.09-5.92 (m, 1H), 5.41-5.31 (m, 1H), 5.31-5.24 (m, 1H), 5.08 (s, 1H), 4.34-4.18 (m, 4H), 3.67-3.53 (m, 2H), 3.27-3.12 (m, 2H), 2.76 (s, 3H), 1.31 (t, J=7.1 Hz, 3H), 1.07 (s, 9H). LCMS (M+H)=543.5.

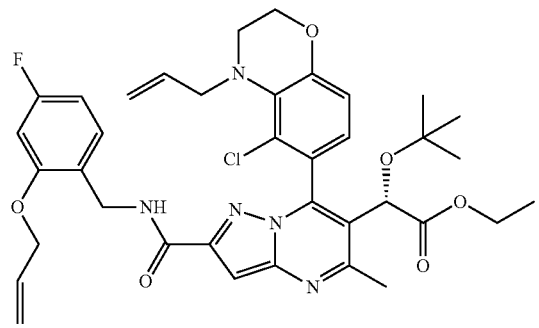 [SMILES: C=CCOc1cc(F)ccc1CNC(=O)c1cc2nc(C)c([C@H](OC(C)(C)C)C(=O)OCC)c(-c3ccc4c(c3Cl)N(CC=C)CCO4)n2n1]

(2S)-Ethyl 2-(7-(4-allyl-5-chloro-3,4-dihydro-2H-benzo[b][1,4]oxazin-6-yl)-2-((2-(allyloxy)-4-fluorobenzyl)carbamoyl)-5-methylpyrazolo[1,5-a]pyrimidin-6-yl)-2-(tert-butoxy)acetate (major atrope isomer)

To a mixture of 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylic acid (50 mg, 0.092 mmol) and (2-(allyloxy)-4-fluorophenyl)methanamine, HCl (40.1 mg, 0.184 mmol) in DMF (1.5 mL) was added DIEA (0.080 mL, 0.460 mmol), HATU (70.0 mg, 0.184 mmol) and DMAP (2.250 mg, 0.018 mmol) and the resulting mixture was stirred at room temp for 16 h. At this point LCMS indicates completion of reaction. Mixture was then purified by prep HPLC to afford (2S)-ethyl 2-(7-(4-allyl-5-chloro-3,4-dihydro-2H-benzo[b][1,4]oxazin-6-yl)-2-((2-(allyloxy)-4-fluorobenzyl)carbamoyl)-5-methylpyrazolo[1,5-a]pyrimidin-6-yl)-2-(tert-butoxy)acetate (37 mg, 0.052 mmol, 56.9% yield) as white solid. $^1$H NMR (500 MHz, CDCl$_3$) δ 7.35 (t, J=6.1 Hz, 1H), 7.28-7.24 (m, 1H), 7.16 (s, 1H), 7.02-6.97 (m, 1H), 6.92 (d, J=8.5 Hz, 1H), 6.64-6.52 (m, 2H), 6.07-5.85 (m, 2H), 5.40-5.31 (m, 2H), 5.27 (t, J=9.0 Hz, 2H), 4.97 (s, 1H), 4.57 (d, J=6.1 Hz, 2H), 4.48 (d, J=5.0 Hz, 2H), 4.26 (d, J=4.1 Hz, 2H), 4.20-4.07 (m, 2H), 3.68-3.54 (m, 2H), 3.24-3.13 (m, 2H), 2.85 (s, 3H), 1.23-1.18 (m, 3H), 1.15 (s, 9H). LCMS (M+H)=706.6.

(2S)-ethyl 2-(7-(4-allyl-5-chloro-3,4-dihydro-2H-benzo[b][1,4]oxazin-6-yl)-2-((2-(allyloxy)-4-fluorobenzyl)carbamoyl)-5-methylpyrazolo[1,5-a]pyrimidin-6-yl)-2-(tert-butoxy)acetate (minor atrope isomer)

Similar to above procedure used to prepare minor atropisomer. (2S)-ethyl 2-(7-(4-allyl-5-chloro-3,4-dihydro-2H-benzo[b][1,4]oxazin-6-yl)-2-((2-(allyloxy)-4-fluorobenzyl)carbamoyl)-5-methylpyrazolo[1,5-a]pyrimidin-6-yl)-2-(tert-butoxy)acetate (75 mg, 0.106 mmol, 57.7% yield) as white solid. $^1$H NMR (500 MHz, CDCl$_3$) δ 7.35-7.30 (m, 1H), 7.27 (dd, J=8.4, 6.8 Hz, 1H), 7.20 (d, J=8.5 Hz, 1H), 7.18-7.15 (m, 1H), 7.03-6.98 (m, 1H), 6.64-6.53 (m, 2H), 6.06-5.86 (m, 2H), 5.39-5.22 (m, 4H), 5.05-5.01 (m, 1H), 4.66-4.53 (m, 2H), 4.52-4.44 (m, 2H), 4.31-4.13 (m, 4H), 3.51 (d, J=5.4 Hz, 2H), 3.20-3.14 (m, 2H), 2.73 (s, 3H), 1.34-1.27 (m, 3H), 1.05 (s, 9H). LCMS (M+H)=706.5.

Example 2 and 3

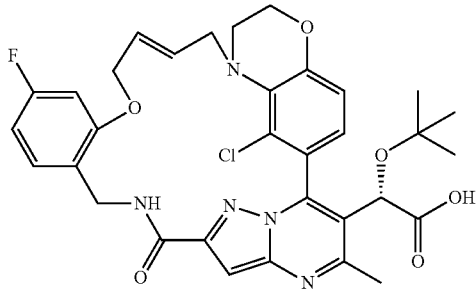

First eluting
Example 2

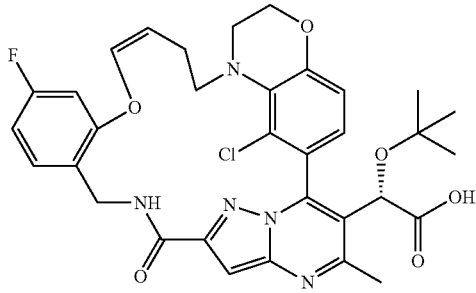

Second eluting
Example 3
major atrope isomer

A mixture of (2S)-ethyl 2-(7-(4-allyl-5-chloro-3,4-dihydro-2H-benzo[b][1,4]oxazin-6-yl)-2-((2-(allyloxy)-4-fluorobenzyl)carbamoyl)-5-methylpyrazolo[1,5-a]pyrimidin-6-yl)-2-(tert-butoxy)acetate (40 mg, 0.057 mmol) and Hoveyda-GrubbsII (4.81 mg, 5.66 µmol) catalyst in DCE (1 mL) was heated to reflux for 3 h. At this point LCMS indicates completion of reaction. Mixture was then cooled to room temp and concentrated under reduced pressure. Mixture was then filtered and purified by prep HPLC to afford cis and trans isomers.

First eluting on HPLC: $^1$H NMR (500 MHz, CDCl$_3$) δ 7.31 (dd, J=8.3, 6.7 Hz, 1H), 7.17 (s, 1H), 6.98-6.95 (m, 1H), 6.87 (d, J=8.4 Hz, 1H), 6.62 (td, J=8.3, 2.4 Hz, 1H), 6.53 (dd, J=10.6, 2.4 Hz, 1H), 6.01-5.90 (m, 1H), 5.74 (dt, J=15.8, 5.2 Hz, 1H), 5.04 (s, 1H), 4.87 (dd, J=15.7, 7.3 Hz, 1H), 4.66-4.55 (m, 2H), 4.53-4.47 (m, 2H), 4.40-4.27 (m, 2H), 4.18-4.03 (m, 3H), 3.54-3.42 (m, 3H), 2.84 (s, 3H), 1.24-1.19 (m, 3H), 1.19 (s, 9H). LCMS (M+H)=678.5.

Second eluting on HPLC: $^1$H NMR (500 MHz, CDCl$_3$) δ 7.52-7.44 (m, 2H), 7.10 (s, 1H), 6.98 (d, J=8.5 Hz, 1H), 6.92 (d, J=8.5 Hz, 1H), 6.76 (td, J=8.3, 2.5 Hz, 1H), 6.69 (dd, J=9.9, 2.5 Hz, 1H), 6.32 (dd, J=6.3, 1.1 Hz, 1H), 5.18 (s, 1H), 4.91 (dt, J=9.3, 5.9 Hz, 1H), 4.65 (dd, J=14.0, 7.1 Hz, 1H), 4.43-4.29 (m, 4H), 4.17-4.01 (m, 2H), 3.47-3.30 (m, 2H), 3.15 (ddd, J=14.1, 11.2, 5.6 Hz, 1H), 2.85 (s, 3H), 2.60-2.41 (m, 2H), 1.22 (s, 9H), 1.17-1.12 (m, 3H). LCMS (M+H)=678.6.

Both cis and trans isomers were treated with 1N NaOH (0.170 mL, 0.170 mmol) in MeOH (1.000 mL) at 50° C. for 3 h. After cooling to room temp, mixture was purified by prep HPLC to afford Example 2

(2S)-2-(tert-Butoxy)-2-[(21E)-31-chloro-16-fluoro-4-methyl-10-oxo-19,27-dioxa-5,7,8,11,24-pentaaza-hexacyclo[22.6.2.1$^{6,9}$.0$^{2,7}$.0$^{13,18}$.0$^{28,32}$]tritriaconta-1(30), 2,4,6(33),8,13(18),14,16,21,28,31-undecaen-3-yl]acetic acid First eluting on HPLC, (6 mg, 9.23 µmol, 16.29% yield) as off-white solid. $^1$H NMR (500 MHz, CDCl$_3$) δ 7.58 (t, J=6.1 Hz, 1H), 7.31 (dd, J=8.4, 6.8 Hz, 1H), 7.20 (s, 1H), 6.92 (d, J=8.4 Hz, 1H), 6.79 (d, J=8.4 Hz, 1H), 6.62 (td, J=8.4, 2.4 Hz, 1H), 6.53 (dd, J=10.6, 2.4 Hz, 1H), 6.00-5.88 (m, 1H), 5.77 (dt, J=15.7, 5.1 Hz, 1H), 5.20 (s, 1H), 4.85 (dd, J=15.7, 7.3 Hz, 1H), 4.64 (dd, J=14.0, 7.2 Hz, 1H), 4.58-4.45 (m, 3H), 4.30 (d, J=11.7 Hz, 2H), 3.53-3.33 (m, 3H), 2.85 (s, 3H), 1.16 (s, 9H). LCMS (M+H)=650.5.

Example 3

(2S)-2-(tert-Butoxy)-2-[(20Z)-31-chloro-16-fluoro-4-methyl-10-oxo-19,27-dioxa-5,7,8,11,24-pentaaza-hexacyclo[22.6.2.1$^{6,9}$.0$^{2,7}$.0$^{13,18}$.0$^{28,32}$]tritriaconta-1(30),2,4,6(33),8,13(18),14,16,20,28,31-undecaen-3-yl]acetic acid Second eluting on HPLC, (5.5 mg, 8.04 µmol, 14.19% yield) as off-white solid. $^1$H NMR (500 MHz, CDCl$_3$) δ 7.52 (t, J=6.5 Hz, 1H), 7.47 (dd, J=8.4, 6.6 Hz, 1H), 7.13 (s, 1H), 6.92 (d, J=8.2 Hz, 1H), 6.83 (d, J=8.4 Hz, 1H), 6.76 (td, J=8.3, 2.5 Hz, 1H), 6.69 (dd, J=9.9, 2.4 Hz, 1H), 6.31 (d, J=6.1 Hz, 1H), 5.26 (s, 1H), 4.91 (dt, J=9.1, 6.0 Hz, 1H), 4.66 (dd, J=14.0, 7.0 Hz, 1H), 4.37-4.21 (m, 3H), 3.66 (d, J=9.8 Hz, 1H), 3.38 (d, J=13.7 Hz, 1H), 3.26 (d, J=9.1 Hz, 1H), 3.19-3.07 (m, 1H), 2.86 (s, 3H), 2.60-2.44 (m, 2H), 1.14 (s, 9H). LCMS (M+H)=650.5.

Example 4 and 5

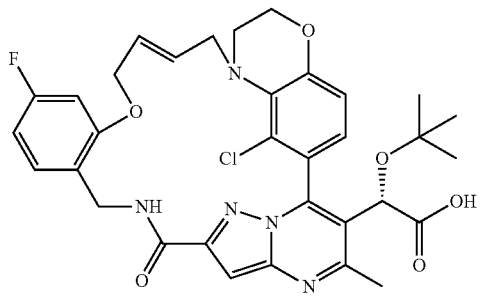 [SMILES: Cc1nc2cc3nn2c(c1[C@H](OC(C)(C)C)C(=O)O)-c1ccc2c(c1Cl)N(CCCCOc1cc(F)ccc1CNC3=O)CCO2]

First eluting
Example 4

-continued

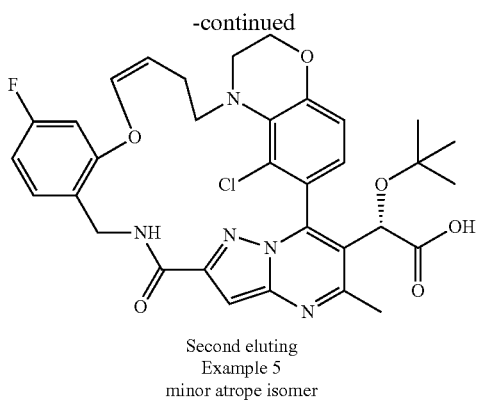

Second eluting
Example 5
minor atrope isomer

Similar procedure was used to prepare minor atrope isomer.

Example 4

(2S)-2-(tert-Butoxy)-2-[(21E)-31-chloro-16-fluoro-4-methyl-10-oxo-19,27-dioxa-5,7,8,11,24-pentaaza-hexacyclo[22.6.2.1$^{6,9}$.0$^{2,7}$.0$^{13,18}$.0$^{28,32}$]tritriaconta-1(30),2,4,6(33),8,13(18),14,16,21,28,31-undecaen-3-yl]acetic acid First eluting acid Product 1 (15 mg, 0.022 mmol, 22.11% yield). $^1$H NMR (500 MHz, CDCl$_3$) δ 7.55-7.51 (m, 1H), 7.38 (d, J=8.5 Hz, 1H), 7.33 (dd, J=8.3, 6.7 Hz, 1H), 7.20 (s, 1H), 6.99 (d, J=8.4 Hz, 1H), 6.62 (td, J=8.4, 2.4 Hz, 1H), 6.54 (dd, J=10.6, 2.4 Hz, 1H), 6.04-5.95 (m, 1H), 5.92-5.85 (m, 1H), 5.15 (s, 1H), 4.97 (dd, J=15.9, 6.3 Hz, 1H), 4.68 (dd, J=14.0, 7.5 Hz, 1H), 4.60 (dd, J=12.8, 4.0 Hz, 1H), 4.52-4.45 (m, 2H), 4.41-4.29 (m, 2H), 3.58-3.52 (m, 1H), 3.52 (s, 3H), 3.51-3.43 (m, 2H), 2.72 (s, 3H), 1.10 (s, 9H). LCMS (M+H)=650.4.

Example 5

(2S)-2-(tert-Butoxy)-2-[(20Z)-31-chloro-16-fluoro-4-methyl-10-oxo-19,27-dioxa-5,7,8,11,24-pentaaza-hexacyclo[22.6.2.1$^{6,9}$.0$^{2,7}$.0$^{13,18}$.0$^{28,32}$]tritriaconta-1(30),2,4,6(33),8,13(18),14,16,20,28,31-undecaen-3-yl]acetic acid Second eluting acid Product 2 (7 mg, 10.23 µmol, 10.32% yield). $^1$H NMR (500 MHz, CDCl$_3$) δ 7.54 (d, J=8.5 Hz, 1H), 7.49 (dd, J=8.0, 7.2 Hz, 1H), 7.19-7.15 (m, 1H), 7.14 (s, 1H), 7.03 (d, J=8.4 Hz, 1H), 6.65 (td, J=8.3, 2.4 Hz, 1H), 6.59 (dd, J=10.9, 2.4 Hz, 1H), 6.26-6.15 (m, 2H), 5.46 (s, 1H), 4.78-4.71 (m, 1H), 4.64 (dd, J=13.9, 6.8 Hz, 1H), 4.48-4.39 (m, 2H), 4.38-4.32 (m, 1H), 4.25 (td, J=10.7, 3.5 Hz, 1H), 4.13 (d, J=17.3 Hz, 1H), 3.91 (dd, J=17.3, 6.2 Hz, 1H), 3.37-3.23 (m, 2H), 2.71 (s, 3H), 1.12 (s, 9H). LCMS (M+H)=650.4.

Example 6

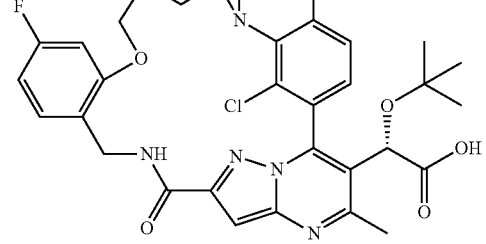

(2S)-2-(tert-Butoxy)-2-{31-chloro-16-fluoro-4-methyl-10-oxo-19,27-dioxa-5,7,8,11,24-pentaaza-hexacyclo[22.6.2.1$^{6,9}$.0$^{2,7}$.0$^{13,18}$.0$^{28,32}$]tritriaconta-1(30), 2,4,6(33),8,13(18),14,16,28,31-decaen-3-yl}acetic acid To a solution of Example 2 (10 mg, 0.015 mmol) in MeOH (1 mL) was added 10% Pd/C (1.637 mg, 1.538 µmol) and the mixture was stirred under balloon hydrogen atmosphere for 30 min. A this point LCMS indicates desired product along with open form. Mixture was then filtered and purified by prep HPLC to afford desired Product 1 (5 mg, 7.28 µmol, 47.4% yield). $^1$H NMR (500 MHz, CDCl$_3$) δ 7.42-7.36 (m, 2H), 7.17-7.16 (m, 1H), 6.93 (d, J=8.4 Hz, 1H), 6.82 (d, J=8.4 Hz, 1H), 6.65-6.56 (m, 2H), 5.22 (s, 1H), 4.58-4.46 (m, 2H), 4.41-4.31 (m, 2H), 4.09-3.99 (m, 3H), 3.48-3.41 (m, 1H), 3.39-3.27 (m, 1H), 2.98-2.89 (m, 1H), 2.86 (s, 3H), 1.97-1.75 (m, 3H), 1.68-1.58 (m, 1H), 1.16 (s, 9H). LCMS (M+H)=652.5.

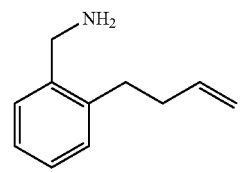

(2-(But-3-en-1-yl)phenyl)methanamine

To a −50° C. solution of 2M LAH (6.36 mL, 12.72 mmol) in THF was added dropwise 2-(but-3-en-1-yl)benzonitrile (2 g, 12.72 mmol) in THF (15 mL) over 15 min. Mixture was then stirred for 3 h, while allowing to warm to room to 0° C. and stirred for 1 h at 0° C. Then cooled in a ice bath and quenched with water (3 mL), 15% NaOH (2 mL) and water (5 mL. Mixture was then filtered and extracted with ethyl acetate, dried (Na$_2$SO$_4$), filtered and concentrated. Crude was then purified by biotage to afford (2-(but-3-en-1-yl)phenyl)methanamine (600 mg, 3.72 mmol, 29.2% yield) as colorless oil. $^1$H NMR (500 MHz, CDCl$_3$) δ 7.39-7.33 (m, 1H), 7.27-7.17 (m, 3H), 5.91 (ddt, J=17.1, 10.3, 6.6 Hz, 1H), 5.09 (dq, J=17.1, 1.7 Hz, 1H), 5.05-4.98 (m, 1H), 3.92 (s, 2H), 2.83-2.75 (m, 2H), 2.43-2.33 (m, 2H). LCMS (M+H)=162.1.

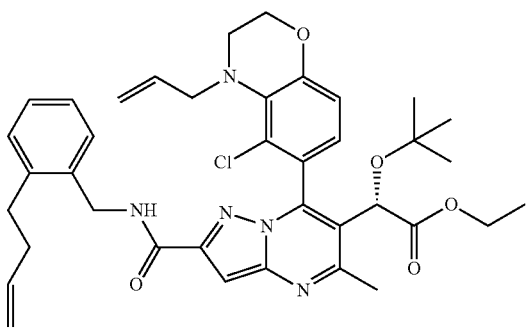 [SMILES: C=CCCc1ccccc1CNC(=O)c1cc2nc(C)c([C@H](OC(C)(C)C)C(=O)OCC)c(-c3ccc4c(c3Cl)N(CC=C)CCO4)n2n1]

(2S)-Ethyl 2-(7-(4-allyl-5-chloro-3,4-dihydro-2H-benzo[b][1,4]oxazin-6-yl)-2-((2-(but-3-en-1-yl)benzyl)carbamoyl)-5-methylpyrazolo[1,5-a]pyrimidin-6-yl)-2-(tert-butoxy)acetate To a mixture of 7-(4-allyl-5-chloro-3,4-dihydro-2H-benzo[b][1,4]oxazin-6-yl)-6-((S)-1-(tert-butoxy)-2-ethoxy-2-oxoethyl)-5-methylpyrazolo[1,5-a]pyrimidine-2-carboxylic acid (50 mg, 0.092 mmol) and (2-(but-3-en-1-yl)phenyl)methanamine (36.4 mg, 0.184 mmol) in DMF (1.5 mL) was added DIEA (0.080 mL, 0.460 mmol), HATU (70.0 mg, 0.184 mmol) and DMAP (2.250 mg, 0.018 mmol) and the resulting mixture was stirred at room temp for 16 h. At this point LCMS indicates completion of reaction. Mixture was then purified by prep HPLC to afford (2S)-ethyl 2-(7-(4-allyl-5-chloro-3,4-dihydro-2H-benzo[b][1,4]oxazin-6-yl)-2-((2-(but-3-en-1-yl)benzyl)carbamoyl)-5-methylpyrazolo[1,5-a]pyrimidin-6-yl)-2-(tert-butoxy)acetate (44 mg, 0.064 mmol, 69.6% yield) as white solid. $^1$H NMR (500 MHz, CDCl$_3$) δ 7.30 (br. s., 1H), 7.26-7.22 (m, 1H), 7.22-7.15 (m, 3H), 7.12-7.06 (m, 1H), 6.97 (d, J=8.4 Hz, 1H), 6.90 (d, J=8.5 Hz, 1H), 6.05-5.94 (m, 1H), 5.81 (ddt, J=17.0, 10.2, 6.7 Hz, 1H), 5.36-5.30 (m, 1H), 5.26 (dd, J=10.2, 1.4 Hz, 1H), 4.99 (s, 1H), 4.98-4.96 (m, 1H), 4.95-4.89 (m, 1H), 4.70-4.58 (m, 2H), 4.29-4.18 (m, 2H), 4.17-4.01 (m, 2H), 3.62-3.45 (m, 2H), 3.16 (t, J=4.4 Hz, 2H), 2.86 (s, 3H), 2.75 (dd, J=8.8, 6.9 Hz, 2H), 2.31 (td, J=7.9, 6.7 Hz, 2H), 1.19 (t, J=7.1 Hz, 3H), 1.16 (s, 9H). LCMS (M+H)=689.6.

Example 7

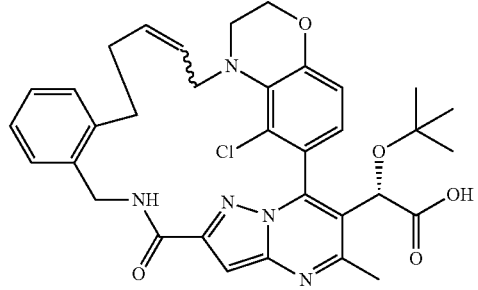 [SMILES: Cc1nc2cc3nn2c(c1[C@H](OC(C)(C)C)C(=O)O)-c1ccc2c(c1Cl)N(CC=CCCc1ccccc1CNC3=O)CCO2]

(2S)-2-(tert-Butoxy)-2-[31-chloro-4-methyl-10-oxo-27-oxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,21,28,31-undecaen-3-yl]acetic acid A mixture of (2S)-ethyl 2-(7-(4-allyl-5-chloro-3,4-dihydro-2H-benzo[b][1,4]oxazin-6-yl)-2-((2-(but-3-en-1-yl) benzyl)carbamoyl)-5-methylpyrazolo[1,5-a]pyrimidin-6-yl)-2-(tert-butoxy)acetate (44 mg, 0.064 mmol) and Hoveyda-GrubbsII (5.44 mg, 6.41 μmol) catalyst in DCE (2 mL) was heated to reflux for 3 h. At this point LCMS indicates completion of reaction and mixture of two products with same MW (possible cis and tarns). Mixture was then cooled to room temp and concentrated under reduced pressure. Mixture was then filtered and purified by prep HPLC to afford two isomers.

Isomer 1 (geometry of double bond not known). $^1$H NMR (400 MHz, CDCl$_3$) δ 7.72 (dd, J=7.3, 1.5 Hz, 1H), 7.27-7.19 (m, 2H), 7.18 (s, 1H), 7.11 (dd, J=7.3, 1.5 Hz, 1H), 6.93 (d, J=2.8 Hz, 2H), 6.92-6.84 (m, 1H), 5.79 (dt, J=15.4, 5.9 Hz, 1H), 5.40-5.29 (m, 1H), 5.24 (s, 1H), 4.97 (dd, J=14.2, 8.2 Hz, 1H), 4.37-4.31 (m, 1H), 4.26 (dd, J=10.0, 3.3 Hz, 1H), 4.19 (dd, J=14.3, 5.3 Hz, 1H), 4.14-4.00 (m, 2H), 3.72 (ddd, J=14.1, 11.7, 5.4 Hz, 1H), 3.58-3.33 (m, 4H), 3.01-2.89 (m, 1H), 2.86 (s, 3H), 2.41-2.25 (m, 2H), 1.23 (s, 9H), 1.12 (t, J=7.0 Hz, 3H). LCMS (M+H)=658.1.

Isomer 2 (product is impure and NMR is complex. used as is in the next step hydrolysis.). LCMS (M+H)=658.5.

Isomer 1 was treated with 1N NaOH (0.192 mL, 0.192 mmol) in MeOH (2.000 mL) at 50° C. for 3 h. After cooling to room temp, mixture was purified by prep HPLC to afford example 7 (6 mg, 9.52 μmol, 14.85% yield) as white solid. $^1$H NMR (400 MHz, CDCl$_3$) δ 7.72 (d, J=7.3 Hz, 1H), 7.26-7.19 (m, 3H), 7.12 (d, J=7.0 Hz, 1H), 6.96-6.86 (m, 2H), 6.85-6.78 (m, 1H), 5.83-5.73 (m, 1H), 5.40-5.31 (m, 1H), 5.29 (s, 1H), 4.97 (dd, J=13.9, 7.9 Hz, 1H), 4.33-4.14 (m, 3H), 3.76-3.68 (m, 2H), 3.53 (dd, J=15.9, 6.4 Hz, 2H), 3.37 (d, J=11.0 Hz, 2H), 2.99-2.91 (m, 1H), 2.88 (s, 3H), 2.32-2.25 (m, 2H), 1.15 (s, 9H). LCMS (M+H)=630.4.

Example 8

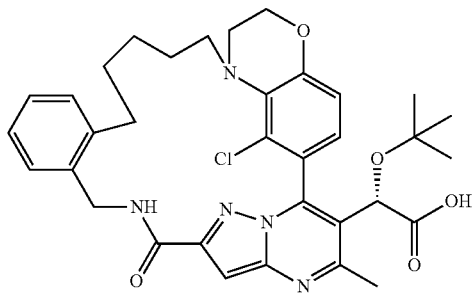 [SMILES: Cc1nc2cc3nn2c(c1[C@H](OC(C)(C)C)C(=O)O)-c1ccc2c(c1Cl)N(CCCCCc1ccccc1CNC3=O)CCO2]

(2S)-2-(tert-Butoxy)-2-{31-chloro-4-methyl-10-oxo-27-oxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,28,31-decaen-3-yl}acetic acid To a solution of Example 7 (10 mg, 0.016 mmol) in MeOH (1 mL) was added 10% Pd/C (1.689 mg, 1.587 μmol) and the mixture was stirred under balloon hydrogen atmosphere for 1 h. A this point LCMS indicates desired product along with open form. Mixture was then filtered and purified by prep HPLC to afford desired Product 1 (2.3 mg, 3.46 μmol, 21.78% yield). $^1$H NMR (400 MHz, CDCl$_3$) δ 7.68-7.62 (m, 1H), 7.25-7.19 (m, 2H), 7.16 (s, 1H), 7.14 (d, J=5.5 Hz, 1H), 7.02 (t, J=6.0 Hz, 1H), 6.90 (d, J=8.3 Hz, 1H), 6.82 (d, J=8.3 Hz, 1H), 5.25 (s, 1H), 4.92 (dd, J=14.2, 7.4 Hz, 1H), 4.29-4.17 (m, 3H), 3.36-3.27 (m, 1H), 3.25-3.00 (m, 3H), 2.86 (s, 3H), 2.80-2.62 (m, 2H), 1.79-1.53 (m, 5H), 1.40-1.25 (m, 1H), 1.13 (s, 9H). LCMS (M+H)=632.5.

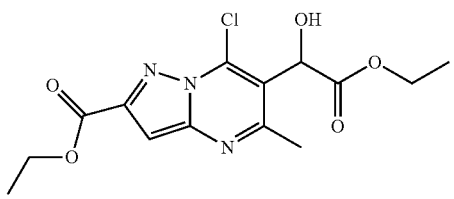

Ethyl 7-chloro-6-(2-ethoxy-1-hydroxy-2-oxoethyl)-5-methylpyrazolo[1,5-a]pyrimidine-2-carboxylate To a stirred solution of 0.9M KHMDS (40.9 mL, 36.8 mmol) in THF (100 mL) at −78° C. was added a THF (50 mL) solution of ethyl 7-chloro-6-(2-ethoxy-2-oxoethyl)-5-methylpyrazolo[1,5-a]pyrimidine-2-carboxylate (10 g, 30.7 mmol) was added over the course of 20 min. After 30 min, a THF (15 mL) solution of 3-phenyl-2-(phenylsulfonyl)-1,2-oxaziridine (10.43 g, 39.9 mmol) was added to the red reaction mixture and stirring was continued for an additional 30 min at −78° C. Then, the resulting orange reaction mixture was quenched with sat. aq. NH$_4$Cl (50 mL), diluted with EtOAc (200 mL), washed with water (100 mL), brine (100 mL), dried (Na$_2$SO$_4$), filtered and concentrated in vacuo to give a solid. This solid was triturated with small amount of ethyl acetate and solids were filtered, washed with hexanes and dried under high vacuum to afford ethyl 7-chloro-6-(2-ethoxy-1-hydroxy-2-oxoethyl)-5-methylpyrazolo[1,5-a]pyrimidine-2-carboxylate (5 g, 16.85 mmol, 43% yield, 90% pure) as light yellow solid. $^1$H NMR (400 MHz, CDCl$_3$) δ 7.21 (s, 1H), 5.76 (s, 1H), 4.58-4.49 (m, 2H), 4.33 (dtt, J=10.7, 7.1, 3.7 Hz, 2H), 2.71-2.64 (s, 3H), 1.48 (t, J=7.2 Hz, 3H), 1.29-1.24 (m, 3H). LCMS (M+1)=342.16.

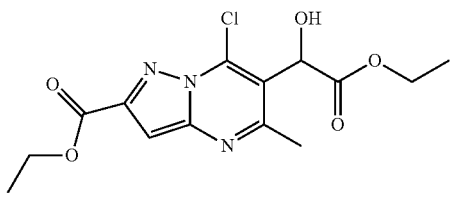

Ethyl 6-(2-ethoxy-2-oxoacetyl)-7-chloro-5-methylpyrazolo[1,5-a]pyrimidine-2-carboxylate To a mixture of 7-chloro-6-(2-ethoxy-1-hydroxy-2-oxoethyl)-5-methylpyrazolo[1,5-a]pyrimidine-2-carboxylate (5.9 g 13.81 mmol) in CH$_2$Cl$_2$ (100 mL) was added Dess-Martin (5.86 g, 13.81 mmol) and the resulting mixture was stirred at rt for 1 h. The reaction mixture was diluted with ethyl acetate (100 mL) and washed with sat. aq. NaHCO$_3$ solution (30 mL), dried (Na$_2$SO$_4$), filtered, and concentrated in vacuo. The residue was purified by silica gel chromatography (5-70% EtOAc/hexane) to afford the desired ethyl 7-chloro-6-(2-ethoxy-2-oxoacetyl)-5-methylpyrazolo[1,5-a]pyrimidine-2-carboxylate (3.5 g, 9.27 mmol, 67.1% yield) as an off-white solid. $^1$H NMR (400 MHz, CDCl$_3$) δ 7.24 (s, 1H), 4.56-4.43 (m, 4H), 2.63 (s, 3H), 1.50-1.41 (m, 6H). LCMS (M+1)=340.13.

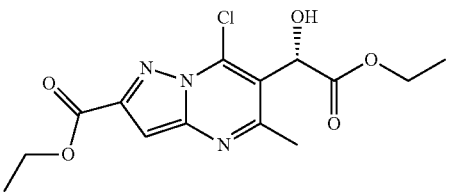 [SMILES: CCOC(=O)c1cc2nc(C)c(C(O)C(=O)OCC)c(Cl)n2n1]

(S)-ethyl 7-chloro-6-(2-ethoxy-1-hydroxy-2-oxoethyl)-5-methylpyrazolo[1,5-a]pyrimidine-2-carboxylate To a stirred yellow solution of ethyl 6-(2-ethoxy-2-oxoacetyl)-7-chloro-5-methylpyrazolo[1,5-a]pyrimidine-2-carboxylate (264 mg, 0.777 mmol) in anhydrous toluene (5 mL) was added 1.0M (R)-1-methyl-3,3-diphenylhexahydropyrrolo[1,2-c][1,3,2]oxazaborole/toluene (0.311 mL, 0.311 mmol). The mixture was cooled to −35° C. and a solution of 50% catechoborane/toluene (0.272 mL, 1.088 mmol) was added over the course of 10 min. After 30 min, the reaction mixture was slowly warmed to −15° C. and stirred for additional 2 h, then diluted with EtOAc (30 mL) and sat. aq. Na$_2$CO$_3$ (5 mL). The mixture was stirred vigorously for 30 min, and the organic phase was washed with sat. aq. Na$_2$CO$_3$ (2×5 mL), dried (Na$_2$SO$_4$), filtered, concentrated. The residue was purified by silica gel chromatography (5-100% EtOAc/hexane) to afford the desired (S)-ethyl 7-chloro-6-(2-ethoxy-1-hydroxy-2-oxoethyl)-5-methylpyrazolo[1,5-a] pyrimidine-2-carboxylate (200 mg, 0.585 mmol, 75% yield) as an off-white solid. $^1$H NMR (400 MHz, CDCl$_3$) δ 7.21 (s, 1H), 5.77 (d, J=2.7 Hz, 1H), 4.53 (d, J=7.1 Hz, 2H), 4.33 (dd, J=7.1, 5.5 Hz, 2H), 3.61 (br. s., 1H), 2.68 (s, 3H), 1.50-1.46 (t, J=7.09 Hz, 3H), 1.28 (t, J=7.09 Hz, 3H). LCMS (M+1)=342.13.

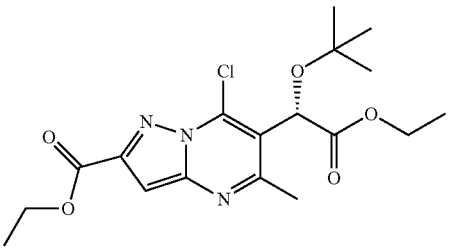 [SMILES: CCOC(=O)c1cc2nc(C)c([C@H](OC(C)(C)C)C(=O)OCC)c(Cl)n2n1]

(S)-Ethyl 6-(1-(tert-butoxy)-2-ethoxy-2-oxoethyl)-7-chloro-5-methylpyrazolo[1,5-a]pyrimidine-2-carboxylate To a stirred solution of (S)-ethyl 7-chloro-6-(2-ethoxy-1-hydroxy-2-oxoethyl)-5-methylpyrazolo[1,5-a]pyrimidine-2-carboxylate (200 mg, 0.585 mmol) in CH$_2$Cl$_2$ (6 mL) and t-butyl acetate (4 mL) at rt was added perchloric acid (0.151 mL, 1.756 mmol). The reaction flask was sealed. After stirring for 3 h, the reaction mixture was diluted with CH$_2$Cl$_2$ (50 mL), carefully quenched with sat. aq. NaHCO$_3$ (5 mL). The organic layer was separated and washed with brine (5 mL), dried (Na$_2$SO$_4$), filtered and concentrated in vacuo to give a yellow liquid. This crude product was purified by flash column chromatography on a silica gel column using (10-50% EtOAc/Hex as eluant) to afford the desired (S)-ethyl 6-(1-(tert-butoxy)-2-ethoxy-2-oxoethyl)-7- chloro-5-methylpyrazolo[1,5-a]pyrimidine-2-carboxylate (200 mg, 0.503 mmol, 86% yield) as viscous oil. ¹H NMR (400 MHz, CDCl₃) δ 7.19 (s, 1H), 5.66 (s, 1H), 4.52 (q, J=7.2 Hz, 2H), 4.25-4.19 (m, 2H), 2.72 (s, 3H), 1.51-1.45 (m, 3H), 1.28 (s, 9H), 1.26-1.21 (m, 3H). LCMS (M+1)=398.25.

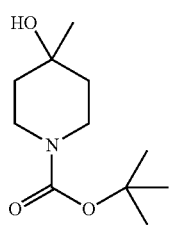

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO₄, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. ¹H NMR (400 MHz, CDCl₃) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

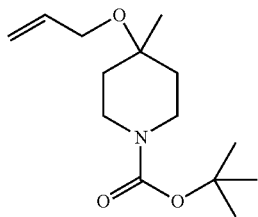 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO₄, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. ¹H NMR (500 MHz, CDCl₃) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

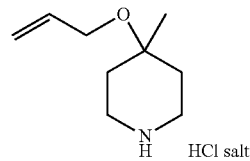

4-(Allyloxy)-4-methylpiperidine hydrogen chloride salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. ¹H NMR (500 MHz, CD₃OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

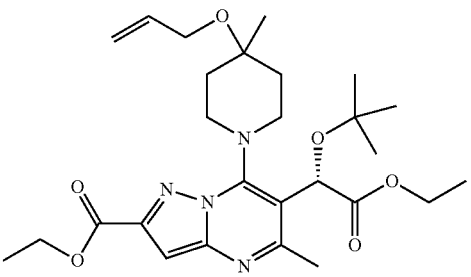 [SMILES: C=CCOC1(C)CCN(c2c([C@H](OC(C)(C)C)C(=O)OCC)c(C)nc3cc(C(=O)OCC)nn23)CC1]

(S)-Ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate A mixture of (S)-ethyl 6-(1-(tert-butoxy)-2-ethoxy-2-oxoethyl)-7-chloro-5-methylpyrazolo[1,5-a]pyrimidine-2-carboxylate (1 g, 2.51 mmol), 4-(allyloxy)-4-methylpiperidine hydrogen chloride salt (0.723 g, 3.77 mmol), Hunig's Base (1.317 mL, 7.54 mmol) in DMF (15 mL) was stirred at rt for 16 h. It was then concentrated and purified by biotage to isolate (S)-ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate (1 g, 69%) as a white solid. ¹H NMR (400 MHz, CDCl₃) δ 7.03 (s, 1H), 6.11-6.01 (m, 1H), 5.86 (br. s., 1H), 5.45 (d, J=17.8 Hz, 1H), 5.22 (dd, J=10.4, 1.6 Hz, 1H), 4.50-4.43 (m, 2H), 4.29-4.18 (m, 2H), 4.06-4.01 (m, 2H), 3.90-3.25 (br. s, 4H), 2.63 (s, 3H), 2.05-1.90 (m, 2H), 1.80-1.69 (m, 1H), 1.66-1.59 (m, 1H), 1.45 (t, J=7.1 Hz, 3H), 1.37 (s, 3H), 1.25-1.21 (m, 12H). LCMS (M+1)=517.43.

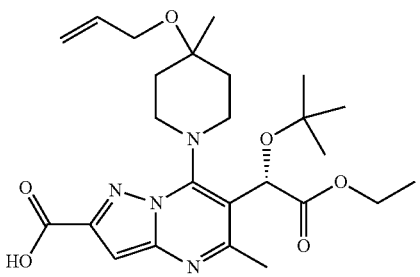 [SMILES: C=CCOC1(C)CCN(c2c([C@H](OC(C)(C)C)C(=O)OCC)c(C)nc3cc(C(=O)O)nn23)CC1]

(S)-7-(4-(Allyloxy)-4-methylpiperidin-1-yl)-6-(1-tert-butoxy-2-ethoxy-2-oxoethyl)-5-methylpyrazolo[1,5-a]pyrimidine-2-carboxylic acid A mixture of (S)-Ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate (1 g, 1.936 mmol), NaOH (1.936 mL, 1.936 mmol) in EtOH (10 mL) was stirred at rt for 16 h. It was then concentrated and adjusted pH=4 by adding 1 N HCl. It was then extracted by EtOAc. The organic layer was dried over MgSO$_4$, filtered and concentrated to obtain (S)-7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylic acid (700 mg, 68%) as a white solid. $^1$H NMR (400 MHz, CDCl$_3$) δ 7.20-7.13 (m, 1H), 6.17-6.00 (m, 1H), 5.99-5.82 (m, 1H), 5.76-5.58 (m, 1H), 5.46 (d, J=17.2 Hz, 2H), 5.31-5.19 (m, 2H), 4.50-3.50 (m, 2H), 4.34-4.12 (m, 2H), 4.08-3.99 (m, 2H), 2.66 (s, 3H), 2.07-1.93 (m, 3H), 1.80-1.65 (m, 1H), 1.37 (s, 2H), 1.31-1.18 (m, 12H) LCMS (M+1)=489.19.

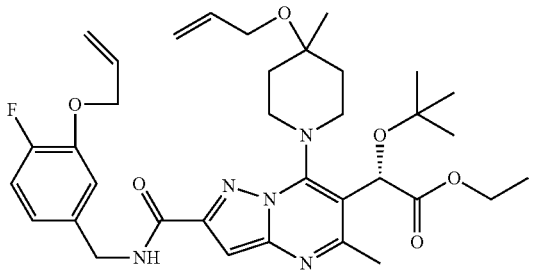 [SMILES: C=CCOc1cc(CNC(=O)c2cc3nc(C)c([C@H](OC(C)(C)C)C(=O)OCC)c(N4CCC(C)(OCC=C)CC4)n3n2)ccc1F]

(S)-Ethyl 2-(2-(3-(allyloxy)-4-fluorobenzylcarbamoyl)-7-(4-(allyloxy)-4-methylpiperidin-1-yl)-5-methylpyrazolo[1,5-a]pyrimidin-6-yl)-2-tert-butoxyacetate A mixture of (S)-7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylic acid (80 mg, 0.164 mmol), HATU (74.7 mg, 0.196 mmol), (2-(allyloxy)-4-fluorophenyl)methanamine hydrogen chloride salt (53.5 mg, 0.246 mmol), Hunig's Base (0.143 mL, 0.819 mmol) in DCM (2 mL) was stirred at rt for 16 h. It was then concentrated and purified by biotage, eluting with 50% EtOAc/hexane to isolate (S)-ethyl 2-(2-(3-(allyloxy)-4-fluorobenzylcarbamoyl)-7-(4-(allyloxy)-4-methylpiperidin-1-yl)-5-methylpyrazolo[1,5-a]pyrimidin-6-yl)-2-tert-butoxyacetate (83 mg, 70%) as a white solid. LCMS (M+1)=652.43.

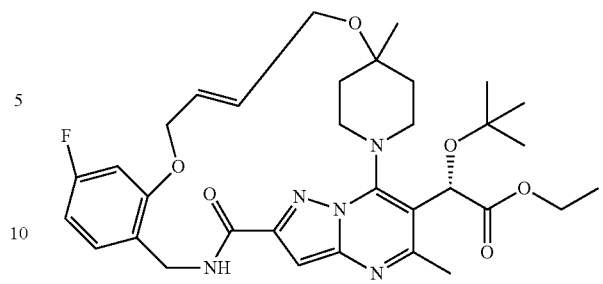

Ethyl (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetate A mixture of (S)-ethyl 2-(2-(3-(allyloxy)-4-fluorobenzylcarbamoyl)-7-(4-(allyloxy)-4-methylpiperidin-1-yl)-5-methylpyrazolo[1,5-a]pyrimidin-6-yl)-2-tert-butoxyacetate (82 mg, 0.126 mmol), (1,3-dimesitylimidazolidin-2-ylidene)(2-isopropoxybenzylidene)ruthenium(VI) chloride (7.88 mg, 0.013 mmol) in ClCH$_2$CH$_2$Cl (30 mL) was heated at 45° C. for 3 h. It was then concentrated and purified by biotage, eluting with 40% EtOac/hexane to isolate ethyl (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetate (80 mg, 100%) as an off-white solid. $^1$H NMR (400 MHz, CDCl$_3$) δ 7.93-7.77 (m, 1H), 7.47-7.43 (m, 1H), 7.09 (s, 1H), 6.68-6.59 (m, 2H), 6.35-6.26 (m, 1H), 6.19-6.11 (m, 1H), 5.99 (s, 1H), 4.80 (dd, J=14.0, 7.7 Hz, 1H), 4.66-4.60 (m, 1H), 4.59-4.43 (m, 3H), 4.28-4.08 (m, 4H), 3.90 (td, J=12.1, 2.4 Hz, 1H), 3.20-3.13 (m, 1H), 2.79 (d, J=11.7 Hz, 1H), 2.69-2.63 (m, 3H), 2.11-2.03 (m, 1H), 1.95 (dd, J=13.7, 2.4 Hz, 1H), 1.82 (td, J=13.2, 4.7 Hz, 1H), 1.73-1.63 (m, 1H), 1.39-1.35 (s, 3H), 1.26 (s, 9H), 1.24-1.21 (m, 3H). LCMS (M+1)=624.42.

Example 9

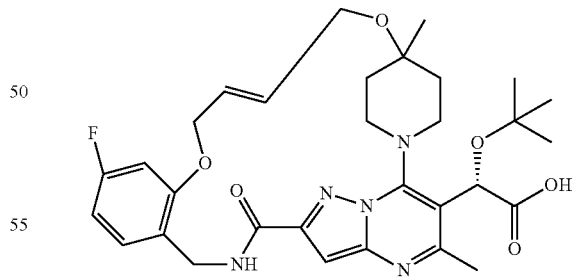

(2S)-2-(tert-Butoxy)-2-[(21E)-16-fluoro-4,25-dimethyl-10-oxo-19,24-dioxa-1,5,7,8,11-pentaazapentacyclo[23.2.2.1$^{6,9}$.0$^2$,$^7$.0$^{13,18}$]triaconta-2,4,6(30),8,13,15,17,21-octaen-3-yl]acetic acid A mixture of ethyl (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetate (80 mg, 0.128 mmol), NaOH (0.641 mL, 0.641 mmol) in EtOH (3 mL) was heated at 60° C. for 4 h. It was then concentrated and adjusted pH=3 using 1 N HCl. It was then extracted with EtOAc, dried over MgSO$_4$, filtered and concentrated to yield 58 mg (72%) of desired product as an off-white solid. $^1$H NMR (400 MHz, CDCl$_3$) δ 7.94-7.83 (m, 1H), 7.45-7.40 (m, 1H), 7.12 (s, 1H), 6.69-6.60 (m, 2H), 6.30 (m, 1H), 6.19-6.09 (m, 1H), 5.98 (br. s., 1H), 4.82 (dd, J=14.1, 8.0 Hz, 1H), 4.67-4.61 (m, 1H), 4.60-4.52 (m, 2H), 4.46 (dd, J=14.1, 5.3 Hz, 1H), 4.16-4.05 (m, 2H), 3.91 (t, J=11.3 Hz, 1H), 3.39 (d, J=10.9 Hz, 1H), 2.82 (d, J=11.5 Hz, 1H), 2.64 (s, 3H), 2.12-2.07 (m, 1H), 2.04-1.94 (m, 1H), 1.76 (td, J=13.2, 4.7 Hz, 1H), 1.66 (td, J=13.4, 4.3 Hz, 1H), 1.36-1.27 (m, 12H). LCMS (M+1)=596.35.

Example 10

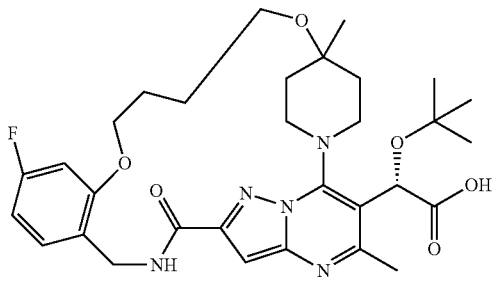 [SMILES: Cc1nc2cc3nn2c(c1[C@H](OC(C)(C)C)C(=O)O)N1CCC(C)(CC1)OCCCCOc1cc(F)ccc1CNC3=O]

(2S)-2-(tert-Butoxy)-2-{16-fluoro-4,25-dimethyl-10-oxo-19,24-dioxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetic acid A mixture of (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid (45 mg, 0.076 mmol), Pd/C (8.04 mg, 7.55 μmol) in MeOH (2 mL) was stirred under a H2 balloon for 6 h. It was then filtered and purified by prep HPLC to isolate (2S)-(16-fluoro-3,8-dimethyl-21-oxo-7,8,10,11,12,13,20,21-octahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid (24 mg, 51%) as a white solid. $^1$H NMR (400 MHz, CDCl$_3$) δ 7.87 (t, J=6.5 Hz, 1H), 7.44-7.38 (m, 1H), 7.12 (s, 1H), 6.68-6.59 (m, 2H), 5.97 (br. s., 1H), 4.76-4.65 (m, 1H), 4.64-4.56 (m, 1H), 4.46 (t, J=11.3 Hz, 1H), 4.13-4.03 (m, 2H), 3.92-3.82 (m, 1H), 3.57-3.48 (m, 2H), 3.37 (d, J=11.8 Hz, 1H), 2.81 (d, J=11.2 Hz, 1H), 2.64 (s, 3H), 2.25-2.01 (m, 6H), 1.98-1.86 (m, 3H), 1.75 (td, J=13.2, 4.8 Hz, 1H), 1.61 (td, J=13.4, 4.4 Hz, 1H), 1.30 (s, 9H). LCMS (M+1)=598.34.

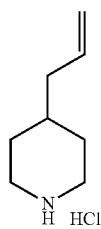

4-Allylpiperidine hydrochloride

A mixture of tert-butyl 4-allylpiperidine-1-carboxylate (1 g, 4.44 mmol), 4M HCl in dioxane (5 mL) was stirred at rt for 3 h. It was then concentrated to obtain 4-allylpiperidine hydrochloride (0.7 g, 98%) as a white solid. $^1$H NMR (400 MHz, CD$_3$OD) δ 5.99-5.66 (m, 1H), 5.14-5.08 (m, 1H), 5.08-5.04 (m, 1H), 3.39 (d, J=12.3 Hz, 2H), 2.98 (t, J=12.3 Hz, 2H), 2.10 (t, J=6.9 Hz, 2H), 1.96 (d, J=13.8 Hz, 2H), 1.77-1.65 (m, 1H), 1.48-1.34 (m, 2H).

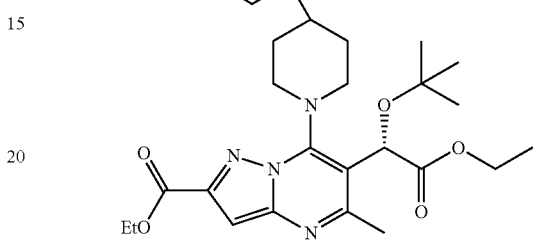

(S)-Ethyl 7-(4-allylpiperidin-1-yl)-6-(1-tert-butoxy-2-ethoxy-2-oxoethyl)-5-methylpyrazolo[1,5-a]pyrimidine-2-carboxylate was prepared following the same procedure to prepare (S)-ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate. $^1$H NMR (400 MHz, CDCl$_3$) δ 7.02 (s, 1H), 6.13-5.69 (m, 2H), 5.18-4.99 (m, 2H), 4.47 (q, J=7.2 Hz, 2H), 4.35-4.02 (m, 3H), 3.70-2.90 (m, 3H), 2.64 (s, 3H), 2.14 (t, J=6.7 Hz, 2H), 1.99-1.80 (m, 2H), 1.75 (br. s., 1H), 1.51-1.41 (m, 3H), 1.41-1.13 (m, 14H). LCMS (M+1)=487.37.

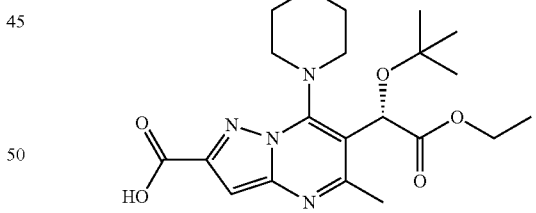

(S)-7-(4-Allylpiperidin-1-yl)-6-(1-tert-butoxy-2-ethoxy-2-oxoethyl)-5-methylpyrazolo[1,5-a]pyrimidine-2-carboxylic acid was prepared following the same procedure to prepare (S)-7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylic acid. $^1$H NMR (400 MHz, CDCl$_3$) δ 7.14 (s, 1H), 6.04-5.75 (m, 2H), 5.18-5.01 (m, 2H), 4.35-4.17 (m, 2H), 4.06 (br. s., 1H), 3.62-3.02 (m, 3H), 2.66 (s, 3H), 2.16 (t, J=6.8 Hz, 2H), 1.95-1.84 (m, 2H), 1.78-1.69 (m, 1H), 1), 1.40-1.21 (m, 14H). LCMS (M+1)=459.34.

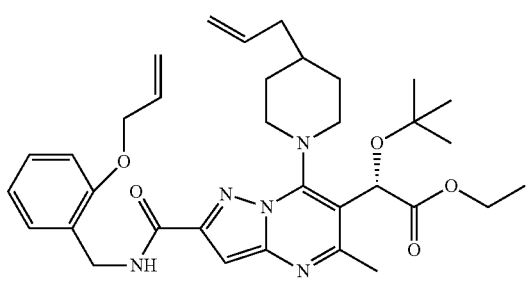

(S)-Ethyl 2-(2-(2-(allyloxy)benzylcarbamoyl)-7-(4-allylpiperidin-1-yl)-5-methylpyrazolo[1,5-a]pyrimidin-6-yl)-2-tert-butoxyacetate It was prepared following the procedure to prepare (S)-ethyl 2-(2-(3-(allyloxy)-4-fluorobenzylcarbamoyl)-7-(4-(allyloxy)-4-methylpiperidin-1-yl)-5-methylpyrazolo[1,5-a]pyrimidin-6-yl)-2-tert-butoxyacetate. $^1$H NMR (400 MHz, CDCl$_3$) δ 7.61 (br. s., 1H), 7.43 (dd, J=7.4, 1.6 Hz, 1H), 7.08 (s, 1H), 7.02-6.95 (m, 1H), 6.92 (d, J=8.2 Hz, 1H), 6.18-6.07 (m, 1H), 5.98 (br. s., 1H), 5.91-5.79 (m, 1H), 5.50 (dd, J=17.3, 1.5 Hz, 1H), 5.31 (dd, J=10.6, 1.4 Hz, 1H), 5.15-5.06 (m, 2H), 4.76 (d, J=6.3 Hz, 2H), 4.66 (dt, J=4.8, 1.6 Hz, 2H), 4.31-4.14 (m, 2H), 4.02 (br. s., 1H), 3.61-3.26 (m, 2H), 3.13 (br. s., 1H), 2.64 (s, 3H), 2.22-2.11 (m, 2H), 1.94-1.80 (m, 2H), 1.70-1.63 (m, 1H), 1.42-1.18 (m, 15H). LCMS (M+1)=604.46.

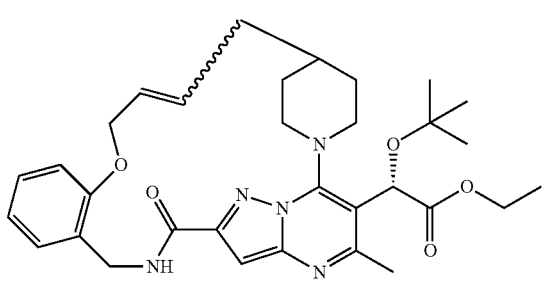 [SMILES: CCOC(=O)[C@@H](OC(C)(C)C)c1c(C)nc2cc3nn2c1N1CCC(CC=CCOc2ccccc2CNC3=O)CC1]

Ethyl (2S)-((10E)-3-methyl-20-oxo-7,8,9,12,19,20-hexahydro-6H,18H-5,8-ethano-21,1-(metheno)pyrimido[6,1-j][1,9,11,12,15]benzoxatetraazacyclooctadecin-4-yl)((2-methyl-2-propanyl)oxy)acetate It was prepared following the same procedure to prepare ethyl (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetate. The product was a mixture of cis/trans isomers. LCMS (M+1)=576.42.

Example 11

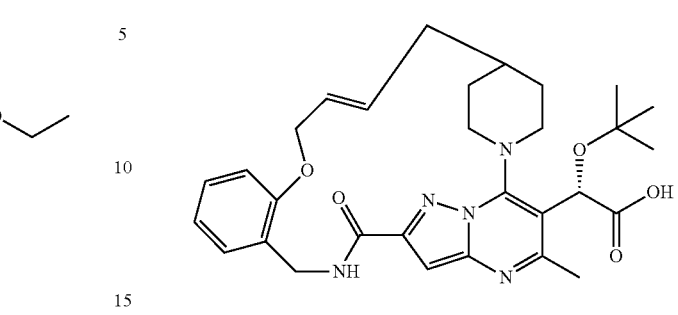

(2S)-2-(tert-Butoxy)-2-[(21E)-4-methyl-10-oxo-19-oxa-1,5,7,8,11-pentaazapentacyclo[22.6.2.1$^{6,9}$.0$^{2,7}$.0$^{13,18}$]nonacosa-2,4,6(29),8,13(18),14,16,21-octaen-3-yl]acetic acid It was prepared following the same procedure as to prepare (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid. $^1$H NMR (400 MHz, CDCl$_3$) δ 7.78 (dd, J=8.5, 3.9 Hz, 1H), 7.47 (d, J=7.3 Hz, 1H), 7.27-7.25 (m, 1H), 7.05 (s, 1H), 6.95 (t, J=7.4 Hz, 1H), 6.84 (d, J=8.2 Hz, 1H), 6.00-5.86 (m, 2H), 5.40 (s, 1H), 4.93 (dd, J=13.6, 9.4 Hz, 1H), 4.51 (d, J=8.7 Hz, 1H), 4.43-4.33 (m, 2H), 4.25 (d, J=11.2 Hz, 1H), 4.10 (d, J=13.2 Hz, 1H), 3.55-3.47 (m, 1H), 3.23 (t, J=11.8 Hz, 1H), 2.58 (s, 3H), 2.52-2.30 (m, 3H), 2.07-1.96 (m, 1H), 1.79-1.64 (m, 3H), 1.27-1.18 (s, 9H). LCMS (M+1)=548.37.

Example 12

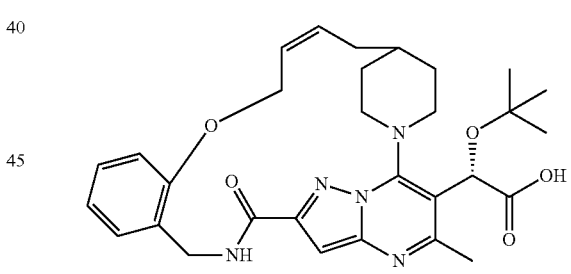

(2S)-2-(tert-Butoxy)-2-[(21Z)-4-methyl-10-oxo-19-oxa-1,5,7,8,11-pentaazapentacyclo[22.6.2.1$^{6,9}$.0$^{2,7}$.0$^{13,18}$]nonacosa-2,4,6(29),8,13(18),14,16,21-octaen-3-yl]acetic acid It was prepared following the same procedure to prepare (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid. $^1$H NMR (400 MHz, CDCl$_3$) δ 7.85 (br. s., 1H), 7.43 (d, J=7.1 Hz, 1H), 7.36-7.31 (m, 1H), 7.09 (s, 1H), 7.03-6.94 (m, 2H), 6.12-5.97 (m, 1H), 5.89-5.78 (m, 1H), 5.40 (s, 1H), 4.80 (dd, J=13.3, 7.8 Hz, 1H), 4.69 (t, J=9.4 Hz, 1H), 4.60 (dd, J=13.6, 3.7 Hz, 1H), 4.55-4.48 (m, 1H), 4.25 (d, J=10.9 Hz, 1H), 4.11 (d, J=12.8 Hz, 1H), 3.51 (t, J=11.2 Hz, 1H), 3.12 (t, J=12.0 Hz, 1H), 2.67-2.57 (m, 3H), 2.55 (m, 1H), 2.39-2.23 (m, 2H), 2.01 (br. s., 1H), 1.81 (d, J=12.8 Hz, 1H), 1.70 (d, J=12.0 Hz, 1H), 1.60 (m, 1H), 1.21 (s, 9H). LCMS (M+1)=548.36.

Example 13

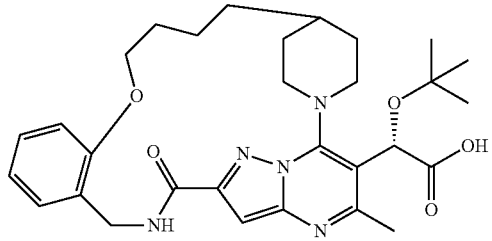 [SMILES: Cc1nc2cc3nn2c(c1[C@H](OC(C)(C)C)C(=O)O)N1CCC(CCCCOc2ccccc2CNC3=O)CC1]

(2S)-2-(tert-Butoxy)-2-{4-methyl-10-oxo-19-oxa-1,5,7,8,11-pentaazapentacyclo[22.6.2.1$^{6,9}$.0$^{2,7}$.0$^{13,18}$]nonacosa-2,4,6(29),8,13(18),14,16-heptaen-3-yl}acetic acid It was prepared following the same procedure to prepare (2S)-(16-fluoro-3,8-dimethyl-21-oxo-7,8,10,11,12,13,20,21-octahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid. $^1$H NMR (400 MHz, CDCl$_3$) δ 7.64 (t, J=6.4 Hz, 1H), 7.51 (d, J=7.3 Hz, 1H), 7.10 (s, 1H), 6.96 (t, J=7.4 Hz, 1H), 6.90 (d, J=8.2 Hz, 1H), 5.49 (d, J=5.2 Hz, 1H), 4.80 (dd, J=13.7, 7.4 Hz, 2H), 4.59 (dd, J=13.7, 6.0 Hz, 1H), 4.19-4.10 (m, 2H), 4.03-3.89 (m, 2H), 3.42 (t, J=11.0 Hz, 1H), 3.22 (t, J=11.7 Hz, 1H), 2.83-2.66 (m, 1H), 2.63 (s, 3H), 2.12-1.93 (m, 2H), 1.93-1.77 (m, 3H), 1.76-1.46 (m, 5H), 1.25 (s, 9H). LCMS (M+1)=550.32.

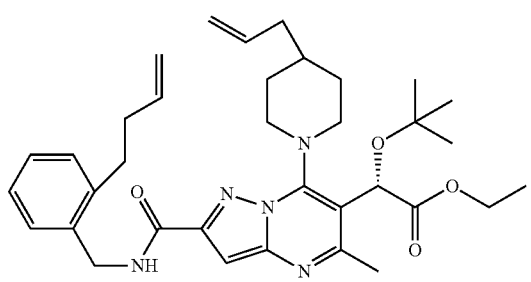 [SMILES: C=CCCc1ccccc1CNC(=O)c1cc2nc(C)c([C@H](OC(C)(C)C)C(=O)OCC)c(N3CCC(CC=C)CC3)n2n1]

(S)-Ethyl 2-(7-(4-allylpiperidin-1-yl)-2-(2-(but-3-enyl)benzylcarbamoyl)-5-methylpyrazolo[1,5-a]pyrimidin-6-yl)-2-tert-butoxyacetate It was prepared following the procedure to prepare (S)-ethyl 2-(2-(3-(allyloxy)-4-fluorobenzylcarbamoyl)-7-(4-(allyloxy)-4-fluoropiperidin-1-yl)-5-methylpyrazolo[1,5-a]pyrimidin-6-yl)-2-tert-butoxyacetate. LCMS (M+1)= 602.47.

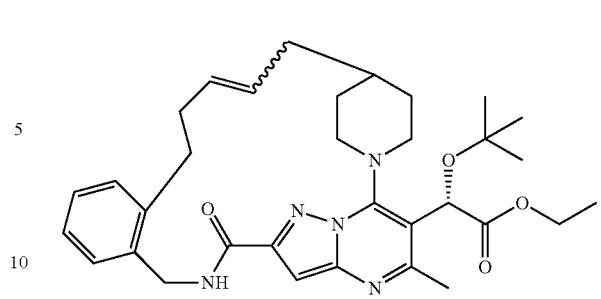

Ethyl (2S)-((10E)-3-methyl-20-oxo-7,8,9,12,13,18,19,20-octahydro-6H-5,8-ethano-21,1-(metheno)pyrimido[1,6-f][2,5,6,8]benzotetraazacyclooctadecin-4-yl)((2-methyl-2-propanyl)oxy)acetate It was prepared following the same procedure to prepare ethyl (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetate. Product is a mixture of cis/trans isomers. LCMS (M+1)=574.42.

Example 14

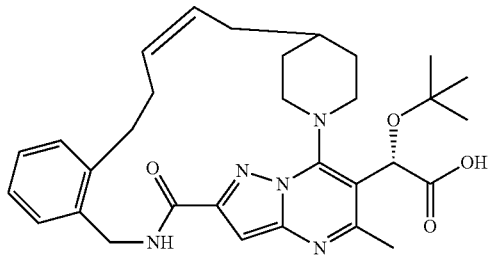 [SMILES: Cc1nc2cc3nn2c(c1[C@H](OC(C)(C)C)C(=O)O)N1CCC(C/C=C\CCc2ccccc2CNC3=O)CC1]

(2S)-tert-Butoxy((21Z)-4-methyl-10-oxo-1,5,7,8,11-pentaazapentacyclo[22.2.2.1~6,9~.0~2,7~.0~13,18~]nonacosa-2,4,6(29),8,13,15,17,21-octaen-3-yl)acetic acid It was prepared following the same procedure to prepare (2S)-((11E)-16-fluoro-3,8-dimethyl-21-oxo-7,8,10,13,20,21-hexahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid. LCMS (M+1)=546.22.

Example 15

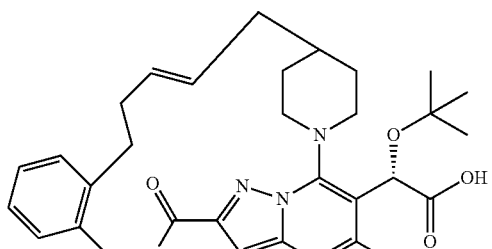

(2S)-2-(tert-Butoxy)-2-[(21Z)-4-methyl-10-oxo-1,5, 7,8,11-pentaazapentacyclo[22.6.2.1$^{6,9}$.0$^{2,7}$.0$^{13,18}$] nonacosa-2,4,6(29),8,13(18),14,16,21-octaen-3-yl] acetic acid It was prepared following the same procedure to prepare (2S)-((11E)-16-fluoro-3,8-dimethyl-21-oxo-7,8,10,13,20, 21-hexahydro-6H,19H-5,8-ethano-22,1-(metheno)pyrimido [6,1-k][1,6,10,12,13,16]benzodioxatetraazacyclononadecin-4-yl)((2-methyl-2-propanyl)oxy)acetic acid. LCMS (M+1)=546.22.

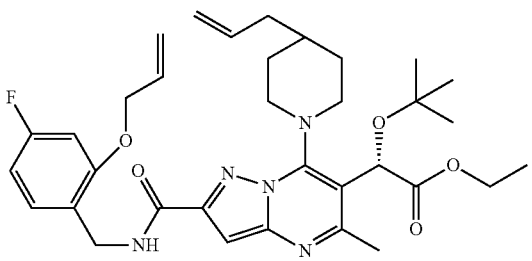 [SMILES: C=CCOc1cc(F)ccc1CNC(=O)c1cc2nc(C)c([C@H](OC(C)(C)C)C(=O)OCC)c(N3CCC(CC=C)CC3)n2n1]

(S)-Ethyl 2-(2-((2-(allyloxy)-4-fluorobenzyl)car-bamoyl)-7-(4-allylpiperidin-1-yl)-5-methylpyrazolo [1,5-a]pyrimidin-6-yl)-2-(tert-butoxy)acetate It was prepared following the procedure to prepare (S)-ethyl 2-(2-(3-(allyloxy)-4-fluorobenzylcarbamoyl)-7-(4-(allyloxy)-4-methylpiperidin-1-yl)-5-methylpyrazolo[1,5-a]pyrimidin-6-yl)-2-tert-butoxyacetate. $^1$H NMR (400 MHz, CDCl$_3$) δ 7.55 (br. s., 1H), 7.42-7.35 (m, 1H), 7.07 (s, 1H), 6.69-6.60 (m, 2H), 6.20-5.92 (m, 2H), 5.91-5.79 (m, 1H), 5.49 (dd, J=17.3, 1.3 Hz, 1H), 5.34 (dd, J=10.6, 1.4 Hz, 1H), 5.16-5.04 (m, 2H), 4.69 (d, J=6.3 Hz, 2H), 4.63 (dt, J=4.9, 1.6 Hz, 2H), 4.29-4.16 (m, 2H), 4.00 (d, J=6.6 Hz, 1H), 3.65-2.99 (m, 3H), 2.64 (s, 3H), 2.15 (t, J=6.9 Hz, 2H), 1.95-1.80 (m, 2H), 1.64 (d, J=10.7 Hz, 1H), 1.53 (d, J=19.2 Hz, 1H), 1.43-1.33 (m, 1H), 1.30-1.22 (m, 12H). LCMS (M+1)=622.46.

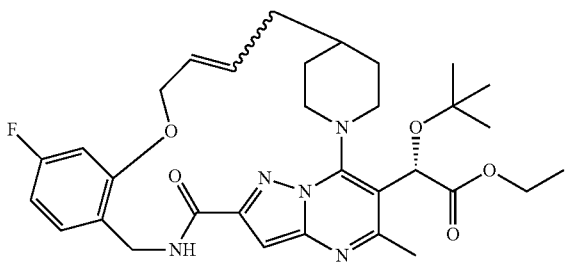 [SMILES: CCOC(=O)[C@@H](OC(C)(C)C)c1c(C)nc2cc3nn2c1N1CCC(CC=CCOc2cc(F)ccc2CNC3=O)CC1]

Ethyl (2S)-((10E)-15-fluoro-3-methyl-20-oxo-7,8,9, 12,19,20-hexahydro-6H,18H-5,8-ethano-21,1-(me-theno)pyrimido[6,1-j][1,9,11,12,15]benzoxatetraaza-cyclooctadecin-4-yl)((2-methyl-2-propanyl)oxy) acetate It was prepared following the same procedure to prepare ethyl (2S)-((11E)-16-fluoro-3,8-dimethyl-21-oxo-7,8,10,13, 20,21-hexahydro-6H,19H-5,8-ethano-22,1-(metheno)py-rimido[6,1-k][1,6,10,12,13,16]benzodioxatetraazacy-clononadecin-4-yl)((2-methyl-2-propanyl)oxy)acetate. LCMS (M+1)=594.44.

Example 16

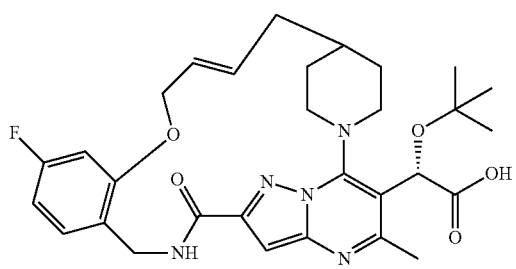 [SMILES: Cc1nc2cc3nn2c(c1[C@H](OC(C)(C)C)C(=O)O)N1CCC(C/C=C/COc2cc(F)ccc2CNC3=O)CC1]

(2S)-2-(tert-Butoxy)-2-[(21E)-16-fluoro-4-methyl-10-oxo-19-oxa-1,5,7,8,11-pentaazapentacyclo [22.6.2.1$^{6,9}$.0$^{2,7}$.0$^{13,18}$]nonacosa-2,4,6(29),8,13(18), 14,16,21-octaen-3-yl]acetic acid It was prepared following the same procedure to prepare (2S)-((11E)-16-fluoro-3,8-dimethyl-21-oxo-7,8,10,13,20, 21-hexahydro-6H,19H-5,8-ethano-22,1-(metheno)pyrimido [6,1-k][1,6,10,12,13,16]benzodioxatetraazacyclononadecin-4-yl)((2-methyl-2-propanyl)oxy)acetic acid. $^1$H NMR (400 MHz, CDCl$_3$) δ 7.86-7.69 (m, 1H), 7.41-7.34 (m, 1H), 7.08 (s, 1H), 6.81-6.61 (m, 2H), 6.13-5.96 (m, 1H), 5.91-5.78 (m, 1H), 5.39 (s, 1H), 4.80-4.46 (m, 4H), 4.25 (d, J=11.0 Hz, 1H), 4.18-4.07 (m, 1H), 3.61-3.45 (m, 2H), 3.25-3.00 (m, 1H), 2.75-2.57 (m, 3H), 2.56-2.45 (m, 1H), 2.36-2.22 (m, 2H), 2.08-1.94 (m, 1H), 1.83 (d, J=14.8 Hz, 1H), 1.71 (d, J=11.8 Hz, 1H), 1.59 (d, J=10.5 Hz, 1H), 1.24-1.12 (s, 9H). LCMS (M+1)=566.30.

Example 17

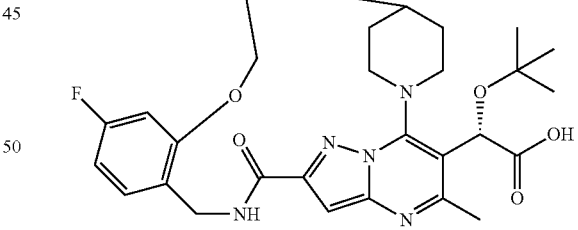

(2S)-2-(tert-Butoxy)-2-[(21Z)-16-fluoro-4-methyl-10-oxo-19-oxa-1,5,7,8,11-pentaazapentacyclo [22.6.2.1$^{6,9}$.0$^{2,7}$.0$^{13,18}$]nonacosa-2,4,6(29),8,13(18), 14,16,21-octaen-3-yl]acetic acid It was prepared following the same procedure to prepare (2S)-((11E)-16-fluoro-3,8-dimethyl-21-oxo-7,8,10,13,20, 21-hexahydro-6H,19H-5,8-ethano-22,1-(metheno)pyrimido [6,1-k][1,6,10,12,13,16]benzodioxatetraazacyclononadecin-4-yl)((2-methyl-2-propanyl)oxy)acetic acid. $^1$H NMR (400 MHz, CDCl$_3$) δ 7.92-7.66 (m, 1H), 7.41 (t, J=7.5 Hz, 1H), 7.06 (s, 1H), 6.70-6.52 (m, 2H), 6.02-5.85 (m, 2H), 5.38 (s, 1H), 4.88 (dd, J=13.2, 9.1 Hz, 1H), 4.48 (d, J=8.2 Hz, 1H), 4.39-4.23 (m, 3H), 4.13 (d, J=11.5 Hz, 1H), 3.58-3.50 (m, 1H), 3.25 (t, J=12.5 Hz, 1H), 2.61 (s, 3H), 2.40 (d, J=13.7 Hz, 3H), 2.10-1.98 (m, 1H), 1.85-1.64 (m, 3H), 1.27-1.12 (m, 10H). LCMS (M+1)=566.38.

Example 18

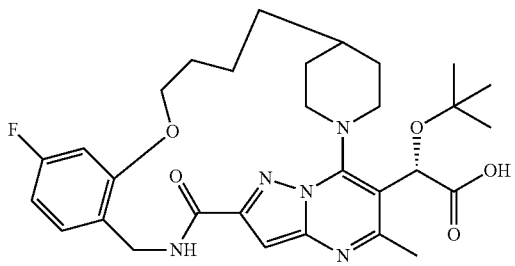 [SMILES: Cc1nc2cc3nn2c(c1[C@H](OC(C)(C)C)C(=O)O)N1CCC(CCCCOc2cc(F)ccc2CNC3=O)CC1]

(2S)-2-(tert-Butoxy)-2-{16-fluoro-4-methyl-10-oxo-19-oxa-1,5,7,8,11-pentaazapentacyclo[22.6.2.1$^{6,9}$.0$^{2,7}$.0$^{13,18}$]nonacosa-2,4,6(29),8,13(18),14,16-heptaen-3-yl}acetic acid It was prepared following the same procedure to prepare (2S)-(16-fluoro-3,8-dimethyl-21-oxo-7,8,10,11,12,13,20,21-octahydro-6H,19H-5,8-ethano-22,1-(metheno)pyrimido[6,1-k][1,6,10,12,13,16]benzodioxatetraazacyclononadecin-4-yl)((2-methyl-2-propanyl)oxy)acetic acid. LCMS (M+1)=568.22.

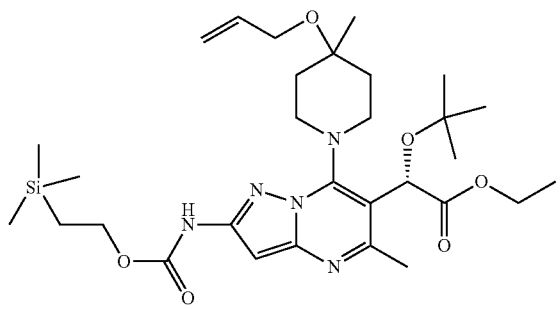 [SMILES: C=CCOC1(C)CCN(c2c([C@H](OC(C)(C)C)C(=O)OCC)c(C)nc3cc(NC(=O)OCC[Si](C)(C)C)nn23)CC1]

(S)-Ethyl 2-(7-(4-(allyloxy)-4-methylpiperidin-1-yl)-5-methyl-2-(((2-(trimethylsilyl)ethoxy)carbonyl)amino)pyrazolo[1,5-a]pyrimidin-6-yl)-2-(tert-butoxy)acetate A mixture (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (600 mg, 1.228 mmol), diphenyl phosphorazidate (0.399 mL, 1.842 mmol), triethylamine (0.257 mL, 1.842 mmol) in toluene (30 mL) was refluxed for 16 h. It was then concentrated in vacuo. The residue was purified by biotage eluting with 20% EtOAc/hexane to isolate 500 mg (61%) of (S)-ethyl 2-(7-(4-(allyloxy)-4-methylpiperidin-1-yl)-5-methyl-2-(((2-(trimethylsilyl)ethoxy)carbonyl)amino)pyrazolo[1,5-a]pyrimidin-6-yl)-2-(tert-butoxy)acetate as an off-white solid. $^1$H NMR (400 MHz, CDCl$_3$) δ 7.22-7.12 (m, 1H), 6.76 (br. s., 1H), 6.17-5.98 (m, 1H), 5.98-5.79 (m, 1H), 5.60-5.41 (m, 1H), 5.24 (d, J=9.9 Hz, 1H), 4.40-4.30 (m, 2H), 4.28-4.14 (m, 2H), 4.02 (d, J=5.0 Hz, 2H), 4.00-3.00 (m, 1H), 3.52 (d, J=5.5 Hz, 1H), 2.60 (s, 3H), 2.05-1.88 (m, 2H), 1.69 (br. s., 1H), 1.63 (s, 1H), 1.41-1.32 (br. s., 3H), 1.31-1.19 (m, 14H), 1.16-1.08 (m, 2H), 0.10 (s, 9H). LCMS (M+1)=604.39.

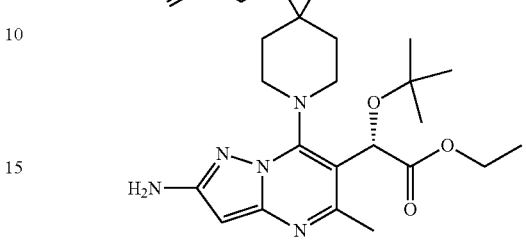

(S)-Ethyl 2-(7-(4-(allyloxy)-4-methylpiperidin-1-yl)-2-amino-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-5-methyl-2-(((2-(trimethylsilyl)ethoxy)carbonyl)amino)pyrazolo[1,5-a]pyrimidin-6-yl)-2-(tert-butoxy)acetate (670 mg, 1.110 mmol), TBAF (1.442 mL, 1.442 mmol) in THF (10 mL) was stirred at rt for 3 h. It was then concentrated and diluted with EtOAc. The organic layer was washed with water, dried over MgSO$_4$, filtered and concentrated to isolate 460 mg (90%) of (S)-ethyl 2-(7-(4-(allyloxy)-4-methylpiperidin-1-yl)-2-amino-5-methylpyrazolo[1,5-a]pyrimidin-6-yl)-2-(tert-butoxy)acetate as a white foam. $^1$H NMR (400 MHz, CDCl$_3$) δ 6.12-5.97 (m, 1H), 5.83 (br. s., 1H), 5.80 (s, 1H), 5.46 (d, J=16.1 Hz, 1H), 5.22 (d, J=10.4 Hz, 1H), 4.35-4.11 (m, 3H), 4.02 (d, J=4.7 Hz, 3H), 3.49-3.35 (m, 2H), 2.58 (br. s., 3H), 2.03-1.88 (m, 3H), 1.50 (m, 1H), 1.35 (br. s., 3H), 1.27-1.19 (m, 12H). LCMS (M+1)=460.13.

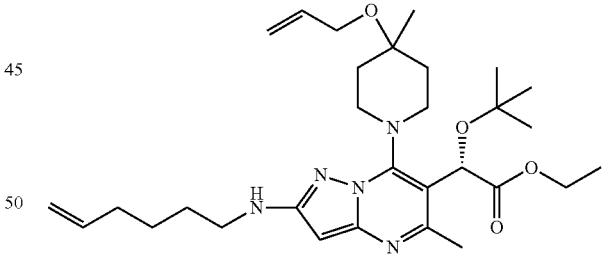

(S)-Ethyl 2-(7-(4-(allyloxy)-4-methylpiperidin-1-yl)-2-(hex-5-en-1-ylamino)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-amino-5-methylpyrazolo[1,5-a]pyrimidin-6-yl)-2-(tert-butoxy)acetate (30 mg, 0.065 mmol), hex-5-enal (6.41 mg, 0.065 mmol), acetic acid (0.019 mL, 0.326 mmol), sodium cyanoborohydride (20.51 mg, 0.326 mmol) in MeOH (2 mL) was stirred at rt for 2 h. LC-MS: still a lot of SM. It was then added another 1 eq of hex-5-enal (6.41 mg, 0.065 mmol) and then stirred at rt for another 1 h, still some SM. It was then added another 1 eq of hex-5-enal (6.41 mg, 0.065 mmol). LC-MS: the reaction was complete. It was then concentrated and purified by biotage, eluting with 40% EtOAc/hexane to isolate 20 mg (57%) of (S)-ethyl 2-(7-(4-(allyloxy)-4-methylpiperidin-1-yl)-2-(hex-5-en-1-ylamino)-5-methylpyrazolo[1,5-a]pyrimidin-6-yl)-2-(tert-butoxy)acetate as a yellow solid. LCMS (M+1)=542.29.

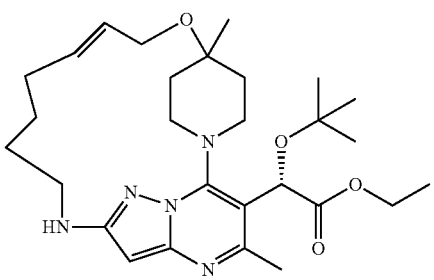 [SMILES: CCOC(=O)[C@@H](OC(C)(C)C)c1c(C)nc2cc3nn2c1N1CCC(C)(CC1)OC/C=C/CCCCN3]

Ethyl (2S)-((8E)-12,17-dimethyl-3,4,5,6,7,10,13,14-octahydro-12H-12,15-ethano-2,19-(metheno)pyrimido[6,1-f][1,5,7,8,10]oxatetraazacycloheptadecin-16-yl)((2-methyl-2-propanyl)oxy)acetate A mixture of (S)-ethyl 2-(7-(4-(allyloxy)-4-methylpiperidin-1-yl)-2-(hex-5-en-1-ylamino)-5-methylpyrazolo[1,5-a]pyrimidin-6-yl)-2-(tert-butoxy)acetate (20 mg, 0.037 mmol), (1,3-dimesitylimidazolidin-2-ylidene)(2-isopropoxybenzylidene)ruthenium(VI) chloride (2.313 mg, 3.69 μmol) in DCE (10 mL) was heated at 45° C. for 6 h. It was then concentrated and purified by biotage, eluting with 0-40% EtOAc/hexane to isolate 7 mg (37%) of macro 16 as a yellow solid. LCMS (M+1)=514.28.

Example 19

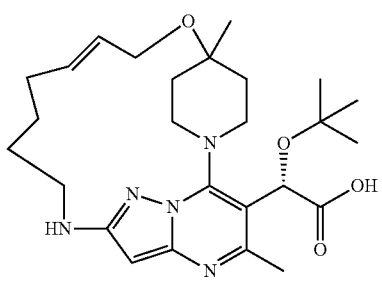 [SMILES: Cc1nc2cc3nn2c(c1[C@H](OC(C)(C)C)C(=O)O)N1CCC(C)(CC1)OC/C=C/CCCCN3]

(2S)-2-(tert-Butoxy)-2-[(15E)-4,19-dimethyl-18-oxa-1,5,7,8,10-pentaazatetracyclo[17.2.2.1$^{6,9}$.0$^{2,7}$]tetracosa-2,4,6(24),8,15-pentaen-3-yl]acetic acid A mixture of macro 16 (7 mg, 0.014 mmol), NaOH (0.1 ml, 0.100 mmol) in EtOH (1 mL) was heated at 60° C. for 3 h. It was then cooled to rt and purified by prep HPLC to isolate 2 mg (29%) of macro 15 as a light yellow solid. LCMS (M+1)=486.21.

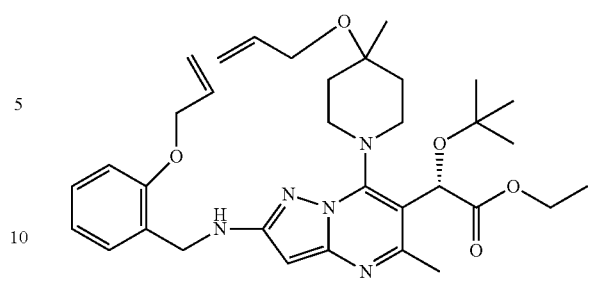

(S)-Ethyl 2-(7-(4-(allyloxy)-4-methylpiperidin-1-yl)-2-((2-(allyloxy)benzyl)amino)-5-methylpyrazolo[1,5-a]pyrimidin-6-yl)-2-(tert-butoxy)acetate was prepared following the procedure to prepare (S)-ethyl 2-(7-(4-(allyloxy)-4-methylpiperidin-1-yl)-2-(hex-5-en-1-ylamino)-5-methylpyrazolo[1,5-a]pyrimidin-6-yl)-2-(tert-butoxy)acetate. $^1$H NMR (400 MHz, CDCl$_3$) δ 7.41 (d, J=6.5 Hz, 1H), 7.23 (td, J=7.8, 1.5 Hz, 1H), 6.96-6.86 (m, 2H), 6.19-5.96 (m, 2H), 5.96-5.65 (m, 2H), 5.59-5.36 (m, 3H), 5.31 (dd, J=10.5, 1.5 Hz, 1H), 5.18 (d, J=10.0 Hz, 1H), 4.80-4.60 (m, 3H), 4.54 (d, J=4.0 Hz, 2H), 4.50-3.50 (m, 3H), 4.29-4.09 (m, 2H), 4.01 (d, J=5.0 Hz, 2H), 2.54 (br. s., 3H), 2.04-1.85 (m, 2H), 1.68 (br. s., 1H), 1.70-1.60 (m, 1H), 1.33 (s, 3H), 1.26-1.14 (m, 12H). LCMS (M+1)=606.22.

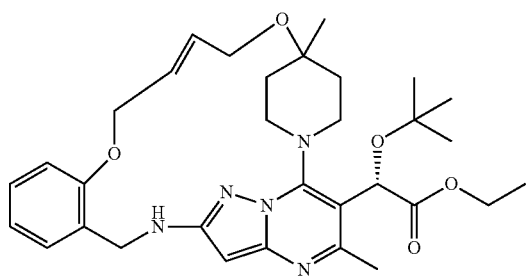 [SMILES: CCOC(=O)[C@@H](OC(C)(C)C)c1c(C)nc2cc3nn2c1N1CCC(C)(CC1)OC/C=C/COc1ccccc1CN3]

Ethyl (2S)-(3,8-dimethyl-7,8,10,13,19,20-hexahydro-6H-5,8-ethano-21,1-(metheno)pyrimido[6,1-k][1,6,10,12,13,15]benzodioxatetraazacyclooctadecin-4-yl)((2-methyl-2-propanyl)oxy)acetate It was prepared following the same procedure to prepare (S)-ethyl 2-(7-(4-(allyloxy)-4-methylpiperidin-1-yl)-2-(hex-5-en-1-ylamino)-5-methylpyrazolo[1,5-a]pyrimidin-6-yl)-2-(tert-butoxy)acetate. LCMS (M+1)=578.37.

Example 20

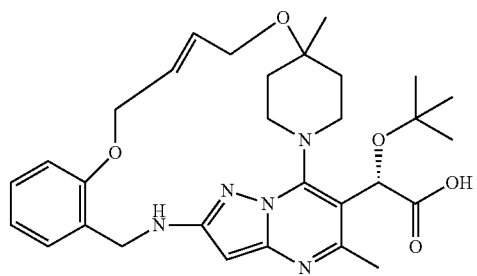 [SMILES: Cc1nc2cc3nn2c(c1[C@H](OC(C)(C)C)C(=O)O)N1CCC(C)(CC1)OC/C=C/COc1ccccc1CN3]

(2S)-2-(tert-Butoxy)-2-[(20E)-4,24-dimethyl-18,23-dioxa-1,5,7,8,10-pentaazapentacyclo[22.2.2.1⁶,⁹.0²,⁷.0¹²,¹⁷]nonacosa-2,4,6(29),8,12(17),13,15,20-octaen-3-yl]acetic acid It was prepared following the procedure to prepare (2S)-((8E)-12,17-dimethyl-3,4,5,6,7,10,13,14-octahydro-12H-12,15-ethano-2,19-(metheno)pyrimido[6,1-f][1,5,7,8,10]oxatetraazacycloheptadecin-16-yl)((2-methyl-2-propanyl)oxy)acetic acid. $^1$H NMR (400 MHz, CDCl$_3$) δ 7.26-7.18 (m, 2H), 6.98-6.90 (m, 2H), 6.30 (br. s., 1H), 6.05-6.00 (m, 2H), 5.62 (s, 1H), 4.90-4.57 (m, 5H), 4.33 (t, J=11.0 Hz, 1H), 4.00 (br. s., 2H), 3.80 (t, J=11.5 Hz, 1H), 3.33 (d, J=8.8 Hz, 1H), 2.71 (s, 3H), 2.02 (d, J=13.8 Hz, 1H), 1.95-1.85 (m, 1H), 1.71 (td, J=12.9, 4.5 Hz, 1H), 1.57-1.46 (m, 1H), 1.29 (m, 12H). LCMS (M+1)=550.25.

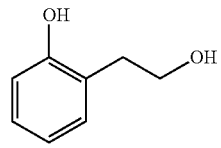

2-(2-Hydroxyethyl)phenol

To a cold (0° C.) solution of 2-(2-hydroxyphenyl)acetic acid (10 g, 65.7 mmol) in THF (150 mL) was added Et$_3$N (10.08 mL, 72.3 mmol) followed by ethyl chloroformate (6.31 mL, 65.7 mmol) dropwise. The mixture was stirred at 0° C. for 1 h and then solids were filtered and the filtrate was added to a cooled (0° C.) solution of NaBH$_4$ (3.73 g, 99 mmol) in 50% aqueous THF. The mixture was stirred at 0° C. for 1 h and then at room temp for 2 h. The solvent was removed in vacuo and the residue was digested in water (200 mL) and ether (500 mL). The ether layer was separated, washed with 2M Na$_2$CO$_3$, water, 1M citric acid and water, dried (Na$_2$SO$_4$), filtered and concentrated to afford 2-(2-hydroxyethyl)phenol (7 g, 50.7 mmol, 77% yield) as colorless oil, which was used in the next step without purification. $^1$H NMR (500 MHz, CDCl$_3$) δ 7.17 (td, J=7.7, 1.7 Hz, 1H), 7.09 (dd, J=7.5, 1.5 Hz, 1H), 6.92 (dd, J=8.0, 1.0 Hz, 1H), 6.88 (td, J=7.4, 1.3 Hz, 1H), 3.98 (dd, J=5.8, 5.0 Hz, 2H), 2.94-2.88 (m, 2H).

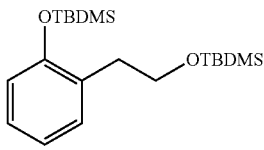 [SMILES: CC(C)(C)[Si](C)(C)OCCc1ccccc1O[Si](C)(C)C(C)(C)C]

tert-Butyl(2-(2-((tert-butyldimethylsilyl)oxy)ethyl)phenoxy)dimethylsilane

To a solution of 2-(2-hydroxyethyl)phenol (6 g, 43.4 mmol) in DMF (150 mL) at 0° C. was added imidazole (8.87 g, 130 mmol) followed by TBDMS-Cl (19.64 g, 130 mmol) and the resulting mixture was stirred at room temp for 72 h. Water (50 mL) was then added and the mixture was extracted with ether (2×200 mL). Ether layer was then washed with brine (50 mL), dried (Na$_2$SO$_4$), filtered and concentrated. The residue was purified by Biotage (0-10% EtOAc/hexane; 300 g column) to afford tert-butyl(2-(2-((tert-butyldimethylsilyl)oxy)ethyl)phenoxy)dimethylsilane (10.4 g, 28.4 mmol, 65.3% yield) as colorless oil. $^1$H NMR (500 MHz, CDCl$_3$) δ 7.19 (d, J=1.7 Hz, 1H), 6.89 (d, J=1.3 Hz, 1H), 6.80 (dd, J=8.0, 1.1 Hz, 1H), 3.81 (t, J=7.3 Hz, 2H), 2.87 (t, J=7.3 Hz, 2H), 1.06 (s, 9H), 0.90 (s, 9H), 0.28 (s, 6H), 0.02 (s, 6H).

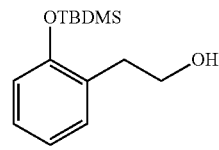 [SMILES: CC(C)(C)[Si](C)(C)Oc1ccccc1CCO]

2-(2-((tert-Butyldimethylsilyl)oxy)phenyl)ethanol

To a solution of tert-butyl(2-(2-((tert-butyldimethylsilyl)oxy)ethyl)phenoxy)dimethylsilane (8.87 g, 24.19 mmol) in ethanol (100 mL) was added PPTS (0.608 g, 2.419 mmol) and the mixture was heated at 50° C. for 1 h. The solvents were then removed and the residue was purified by flash chromatography (5-30% EtOAc/hexane) to afford 2-(2-((tert-butyldimethylsilyl)oxy)phenyl)ethanol (4.4 g, 17.43 mmol, 72.1% yield) as colorless oil. $^1$H NMR (500 MHz, CDCl$_3$) δ 7.20 (dd, J=7.4, 1.6 Hz, 1H), 7.14 (td, J=7.7, 1.7 Hz, 1H), 6.97-6.90 (m, 1H), 6.84 (dd, J=8.1, 1.0 Hz, 1H), 3.86 (q, J=6.5 Hz, 2H), 2.91 (t, J=6.5 Hz, 2H), 1.62 (t, J=5.8 Hz, 1H), 1.05 (s, 9H), 0.28 (s, 6H).

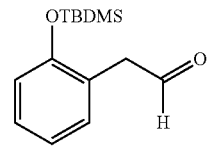 [SMILES: CC(C)(C)[Si](C)(C)Oc1ccccc1CC=O]

2-(2-((tert-Butyldimethylsilyl)oxy)phenyl)acetaldehyde

To a solution of 2-(2-((tert-butyldimethylsilyl)oxy)phenyl)ethanol (4.3 g, 17.03 mmol) in CH$_2$Cl$_2$ (120 mL) at 0° C. was added Dess-Martin periodinane (10.84 g, 25.6 mmol) and the mixture was stirred at 0° C. for 1 h, and then mixture was warmed to room temp and stir for additional 1 h. Mixture was then diluted with CH$_2$Cl$_2$ (100 mL) and washed with sat. NaHCO$_3$ (50 mL) solution, dried (Na$_2$SO$_4$), filtered and concentrated. The residue was then purified by flash chromatography (5-30% EtOAc/hexane) to afford 2-(2-((tert-butyldimethylsilyl)oxy)phenyl)acetaldehyde (3.4 g, 13.58 mmol, 80% yield) as colorless oil. $^1$H NMR (500 MHz, CDCl$_3$) δ 9.72 (t, J=2.2 Hz, 1H), 7.22 (td, J=7.8, 1.8 Hz, 1H), 7.17 (dd, J=7.5, 1.5 Hz, 1H), 7.01-6.94 (m, 1H), 6.90 (dd, J=8.1, 0.9 Hz, 1H), 3.66 (d, J=2.2 Hz, 2H), 1.04 (s, 9H), 0.29 (s, 6H).

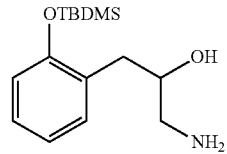

1-Amino-3-(2-((tert-butyldimethylsilyl)oxy)phenyl)propan-2-ol

TMS-CN (2.002 mL, 14.94 mmol) was added dropwise to a mixture of 2-(2-((tert-butyldimethylsilyl)oxy)phenyl)acetaldehyde (3.4 g, 13.58 mmol) and ZnI₂ (0.217 g, 0.679 mmol) in a dry roundbottom flask and the mixture was stirred at room temp for 1 h. The crude cyanohydrin ether was then dissolved in ether (5 mL) and added dropwise to a solution of 2M LAH 2M/THF (7.47 mL, 14.94 mmol) in ether (20 mL) and stirred at room temp for 1 h. Water (1 mL) was then added dropwise, followed by 15% NaOH (1 mL) and then water (2 mL). Mixture was the stirred for 15 min (granular yellow precipitate were formed). Filtration, drying (Na₂SO₄) and concentration gave a 1-amino-3-(2-((tert-butyldimethylsilyl)oxy)phenyl)propan-2-ol (2.2 g, 7.82 mmol, 57.6% yield) as yellow oil, which was used in the next step without further purification. ¹H NMR (500 MHz, CDCl₃) δ 7.19 (dd, J=7.4, 1.7 Hz, 1H), 7.13 (td, J=7.7, 1.7 Hz, 1H), 6.95-6.91 (m, 1H), 6.84 (dd, J=8.1, 1.0 Hz, 1H), 3.85-3.78 (m, 1H), 2.86-2.73 (m, 3H), 2.62 (dd, J=12.9, 7.7 Hz, 1H), 1.06 (s, 9H), 0.29 (s, 6H).

(2S)-Ethyl 2-(7-(4-(allyloxy)-4-methylpiperidin-1-yl)-2-((3-(2-((tert-butyldimethylsilyl)oxy)phenyl)-2-hydroxypropyl)carbamoyl)-5-methylpyrazolo[1,5-a]pyrimidin-6-yl)-2-(tert-butoxy)acetate and (2S)-ethyl 2-(7-(4-(allyloxy)-4-methylpiperidin-1-yl)-2-((2-hydroxy-3-(2-hydroxyphenyl)propyl)carbamoyl)-5-methylpyrazolo[1,5-a]pyrimidin-6-yl)-2-(tert-butoxy)acetate To a solution of (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (2.2 g, 4.50 mmol) in CH₂Cl₂ (30 mL, contains cat. DMF) was added oxalyl chloride (2.477 mL, 4.95 mmol) and the mixture was stirred at room temp for 1 h. The crude acid chloride was then added to a pre-stirred solution of 1-amino-3-(2-((tert-butyldimethylsilyl)oxy)phenyl)propan-2-ol.HCl (1.861 g, 5.85 mmol) and DIEA (3.93 mL, 22.51 mmol) in CH₂Cl₂ (30.0 mL) and the resulting solution was stirred at room temperature for 4 h. Water was then added and the mixture was extracted with dichloromethane, dried (Na₂SO₄), filtered and concentrated. The crude was then purified by flash column chromatography on silica gel column using (5-70% EtOAc/Hex as eluant) to afford (2S)-ethyl 2-(7-(4-(allyloxy)-4-methylpiperidin-1-yl)-2-((3-(2-((tert-butyldimethylsilyl)oxy)phenyl)-2-hydroxypropyl)carbamoyl)-5-methylpyrazolo[1,5-a]pyrimidin-6-yl)-2-(tert-butoxy)acetate (1.7 g, 2.261 mmol, 50.2% yield) as white solid. ¹H NMR (500 MHz, CDCl₃) δ 7.53-7.47 (m, 1H), 7.21 (dt, J=7.4, 1.6 Hz, 1H), 7.18-7.12 (m, 1H), 7.08 (d, J=1.3 Hz, 1H), 6.95 (tt, J=7.4, 1.1 Hz, 1H), 6.87-6.83 (m, 1H), 5.95 (td, J=11.1, 5.2 Hz, 2H), 5.35 (dd, J=17.2, 1.9 Hz, 1H), 5.03 (br. s., 1H), 4.29-4.16 (m, 2H), 4.13-4.07 (m, 1H), 4.03-3.94 (m, 2H), 3.72 (br. s., 2H), 3.53-3.38 (m, 1H), 3.15 (br. s., 1H), 3.09 (br. s., 1H), 2.98-2.82 (m, 3H), 2.64 (s, 3H), 2.06-1.91 (m, 2H), 1.88 (br. s., 1H), 1.69 (d, J=11.5 Hz, 1H), 1.33 (s, 3H), 1.26-1.23 (m, 12H), 1.04 (s, 9H), 0.27 (s, 6H). LCMS (M+H)=753.7 and deprotected phenol (2S)-ethyl 2-(7-(4-(allyloxy)-4-methylpiperidin-1-yl)-2-((2-hydroxy-3-(2-hydroxyphenyl)propyl)carbamoyl)-5-methylpyrazolo[1,5-a]pyrimidin-6-yl)-2-(tert-butoxy)acetate (0.8 g, 1.254 mmol, 27.9% yield) as white solid. ¹H NMR (500 MHz, CDCl3) δ 8.37 (br. s., 1H), 7.20-7.07 (m, 3H), 6.87 (qd, J=7.4, 6.3 Hz, 2H), 6.12-5.94 (m, 2H), 5.45-5.35 (m, 1H), 5.14 (d, J=10.4 Hz, 1H), 4.62 (br. s., 1H), 4.28-4.04 (m, 6H), 3.85-3.73 (m, 1H), 3.62 (ddd, J=14.3, 6.9, 3.4 Hz, 1H), 3.43 (d, J=6.9 Hz, 1H), 3.29 (br. s., 1H), 3.11-2.96 (m, 2H), 2.89 (dd, J=14.1, 6.1 Hz, 1H), 2.85-2.76 (m, 1H), 2.67 (s, 3H), 2.12-1.99 (m, 2H), 1.86 (br. s., 1H), 1.83-1.70 (m, 1H), 1.42 (s, 3H), 1.33-1.18 (m, 12H). LCMS (M+H)=638.7.

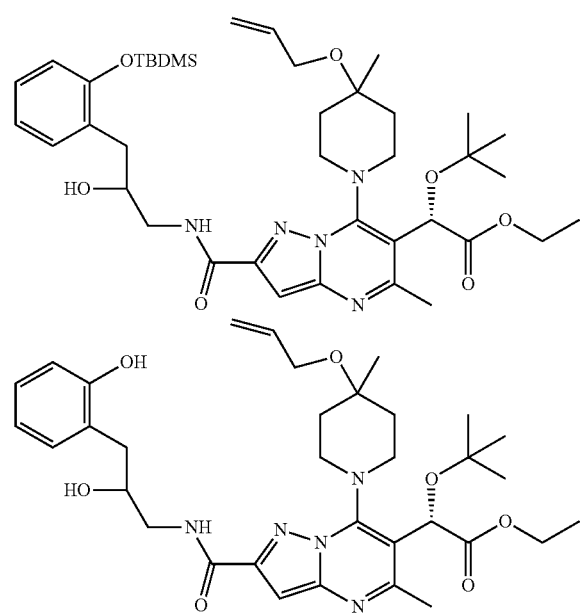

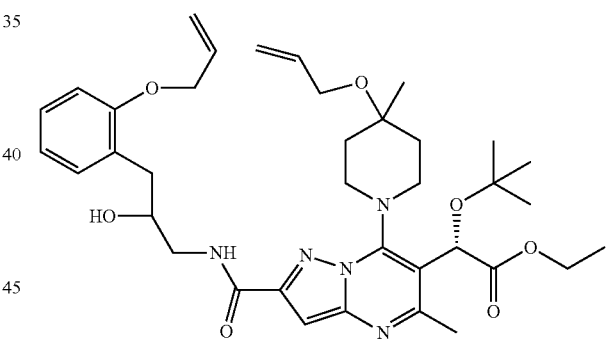

(2S)-Ethyl 2-(7-(4-(allyloxy)-4-methylpiperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate To a solution of (2S)-ethyl 2-(7-(4-(allyloxy)-4-methylpiperidin-1-yl)-2-((2-hydroxy-3-(2-hydroxyphenyl)propyl)carbamoyl)-5-methylpyrazolo[1,5-a]pyrimidin-6-yl)-2-(tert-butoxy)acetate (400 mg, 0.627 mmol) in DMF (6 mL) was added K₂CO₃ (87 mg, 0.627 mmol) and the mixture was heated at 70° C. for 10 min. Mixture was then cooled to room temp and added 3-bromoprop-1-ene (0.064 mL, 0.753 mmol) and the resulting mixture was stirred at room temp for 16 h. Water was then added and the mixture was extracted with ether (2×25 mL), washed with brine (10 mL), dried (Na₂SO₄), filtered and concentrated. The residue was purified by Biotage (0-40% EtOAc/hexane; 40 g column) to afford (2S)-ethyl 2-(7-(4-(allyloxy)-4-methylpiperidin-1- yl)-2-((3-(2-(allyloxy)phenyl)-2-hydroxypropyl)carbamoyl)-5-methylpyrazolo[1,5-a]pyrimidin-6-yl)-2-(tert-butoxy)acetate (310 mg, 0.457 mmol, 72.9% yield) as white solid. $^1$H NMR (500 MHz, CDCl$_3$) δ 7.55-7.50 (m, 1H), 7.26-7.19 (m, 2H), 7.08 (d, J=1.3 Hz, 1H), 6.95 (t, J=7.4 Hz, 1H), 6.90 (d, J=8.0 Hz, 1H), 6.12-6.03 (m, 1H), 6.01-5.79 (m, 2H), 5.47-5.40 (m, 1H), 5.39-5.33 (m, 1H), 5.28 (dd, J=10.6, 1.1 Hz, 1H), 5.04 (br. s., 1H), 4.59 (dt, J=5.1, 1.5 Hz, 2H), 4.31-4.10 (m, 4H), 3.98 (d, J=4.6 Hz, 2H), 3.76 (br. s., 2H), 3.45-3.39 (m, 1H), 3.01-2.83 (m, 2H), 2.64 (s, 3H), 2.04-1.91 (m, 2H), 1.71 (br. s., 1H), 1.34 (s, 3H), 1.26-1.20 (m, 12H), 4 missing protons from piperidine. LCMS (M+H)=678.7.

Example 21 and 22

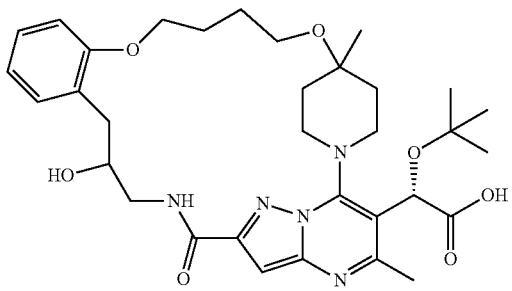

Example 21

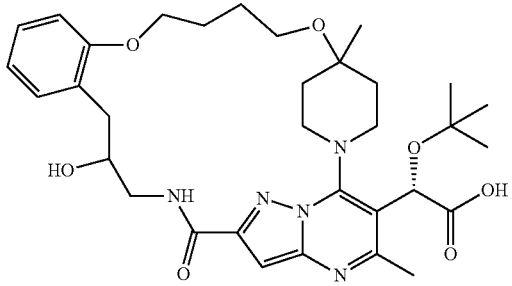

Example 22

(2S)-2-(tert-butoxy)-2-{13-hydroxy-4,27-dimethyl-10-oxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetic acid To a solution of (2S)-ethyl 2-(7-(4-(allyloxy)-4-methyl-piperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate (20 mg, 0.030 mmol) in DCE (5 mL) at 70° C. was added Hoveyda-Grubbs catalyst 2$^{nd}$ generation (1.5 mg) and the mixture was heated at 70° C. for 2 h. At this point LCMS indicated consumption of starting material and desired product as major (cyclized, approx 1:1 mixture of diastereomers). Mixture was cooled and concentrated under reduced pressure. The residue was then diluted with MeOH (2 mL) and added 10% Pd/C (3.14 mg, 0.003 mmol). The mixture was then stirred under balloon hydrogen atmosphere for 1 h. At this point LCMS indicated reduction of double bond. Mixture was then filtered through a pad of celite and the pad was washed with methanol. Filtrate was then concentrated and treated with 1N NaOH (0.148 mL, 0.148 mmol) in MeOH (2 mL) at 70° C. for 2 h. Mixture was then cooled and purified by prep-HPLC to afford two diastereomers.

Example 21

(First eluting on HPLC, 5 mg, 7.46 μmol, 25.3% yield), $^1$H NMR (500 MHz, CDCl$_3$) δ 7.53 (t, J=5.8 Hz, 1H), 7.25-7.18 (m, 2H), 7.11 (s, 1H), 6.94 (t, J=7.5 Hz, 1H), 6.89 (d, J=8.0 Hz, 1H), 5.96 (br. s., 1H), 4.43 (t, J=11.8 Hz, 1H), 4.25-4.11 (m, 4H), 4.00-3.76 (m, 3H), 3.55-3.45 (m, 2H), 3.45-3.27 (m, 2H), 3.11 (dd, J=13.8, 6.2 Hz, 1H), 2.86-2.78 (m, 2H), 2.65 (s, 3H), 2.12-1.98 (m, 3H), 1.93-1.80 (m, 2H), 1.79-1.57 (m, 2H), 1.30 (s, 9H), 1.26 (s, 3H). LCMS (M+H)=624.6.

Example 22

(Second eluting on HPLC, 5 mg, 7.62 μmol, 25.8% yield): $^1$H NMR (500 MHz, CDCl$_3$) δ 7.62 (d, J=5.2 Hz, 1H), 7.27-7.19 (m, 2H), 7.11 (s, 1H), 6.97 (t, J=7.1 Hz, 1H), 6.91 (d, J=8.0 Hz, 1H), 5.94 (br. s., 1H), 4.48 (t, J=12.2 Hz, 1H), 4.21-4.08 (m, 3H), 4.03-3.93 (m, 1H), 3.80 (t, J=11.7 Hz, 1H), 3.56-3.41 (m, 4H), 3.21 (dd, J=14.1, 8.7 Hz, 1H), 2.98 (d, J=12.1 Hz, 1H), 2.82-2.77 (m, 1H), 2.62 (s, 3H), 2.11-2.03 (m, 2H), 2.00-1.94 (m, 2H), 1.92-1.83 (m, 2H), 1.74 (dd, J=12.8, 9.3 Hz, 1H), 1.67-1.56 (m, 1H), 1.33-1.26 (m, 12H). LCMS (M+H)=624.6.

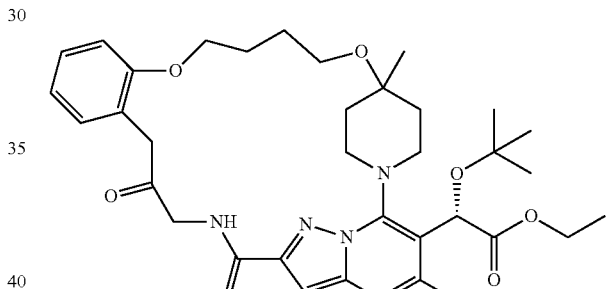

Ethyl (2S)-2-(tert-butoxy)-2-{$^2$1,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetate To a solution of (2S)-ethyl 2-(7-(4-(allyloxy)-4-methyl-piperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate (150 mg, 0.221 mmol) in DCE (30 mL) at 70° C. was added Hoveyda-Grubbs catalyst 2$^{nd}$ generation (11.09 mg, 0.018 mmol) and the mixture was heated at 70° C. for 2 h. At this point LCMS indicated consumption of starting material and presence of desired product as major (cyclized, approx 1:1 mixture of diastereomers). Mixture was then cooled and concentrated under reduced pressure. The residue was then diluted with MeOH (5 mL) and added 10% Pd/C (23.55 mg, 0.022 mmol). The mixture was then stirred under balloon hydrogen atmosphere for 1 h. At this point LCMS indicates reduction of double bond. Mixture was then filtered through a pad of celite and the pad was washed with methanol. Filtrate was then concentrated, dried under high vac. The residue was then diluted with CH$_2$Cl$_2$ (5 mL) and added powdered 4 A° sieves (300 m g) and NMO (38.9 mg, 0.332 mmol). After stirring the mixture for 10 min, TPAP (7.78 mg, 0.022 mmol) was added and the mixture was stirred at room temp for 1 h. Mixture was then filtered through a pad of silica gel and filtrate was concentrated and purified by Biotage (0-30% EtOAc/hexane; 25 g column) to afford ethyl (2S)-2-(tert-butoxy)-2-{4,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetate (62 mg, 0.095 mmol, 43.1% yield) as white solid. $^1$H NMR (500 MHz, CDCl$_3$) δ 7.84 (t, J=5.0 Hz, 1H), 7.32-7.27 (m, 1H), 7.25 (d, J=7.4 Hz, 1H), 7.05 (s, 1H), 6.98 (t, J=7.1 Hz, 1H), 6.87 (d, J=8.0 Hz, 1H), 6.14 (s, 1H), 4.61-4.53 (m, 1H), 4.32 (dd, J=5.0, 3.9 Hz, 2H), 4.26-4.21 (m, 1H), 4.19-4.10 (m, 2H), 4.08-3.94 (m, 2H), 3.73 (d, J=5.0 Hz, 2H), 3.52-3.40 (m, 2H), 2.98 (d, J=11.0 Hz, 1H), 2.74 (d, J=11.2 Hz, 1H), 2.67 (s, 3H), 2.07-2.02 (m, 1H), 1.93 (dd, J=13.6, 2.2 Hz, 1H), 1.88-1.73 (m, 5H), 1.68-1.63 (m, 1H), 1.31 (s, 3H), 1.28 (s, 9H), 1.22 (t, J=7.1 Hz, 3H). LCMS (M+H)=650.6.

Example 23

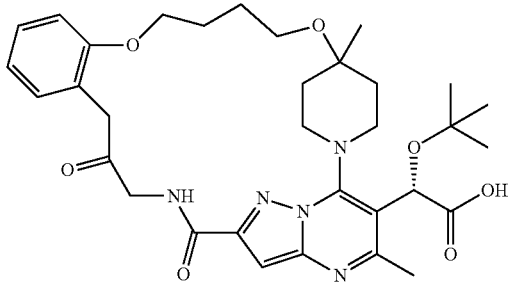 [SMILES: Cc1nc2cc3nn2c(c1[C@H](OC(C)(C)C)C(=O)O)N1CCC(C)(CC1)OCCCCOc1ccccc1CC(=O)CNC3=O]

(2S)-2-(tert-Butoxy)-2-{4,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetic acid To a solution ethyl (2S)-2-(tert-butoxy)-2-{4,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetate (6 mg, 9.23 μmol) in MeOH (0.5 mL) was added 1N NaOH (0.046 mL, 0.046 mmol) and the mixture was heated at 70° C. for 3 h. Mixture was then cooled and purified by prep-HPLC to afford desired product (3.8 mg, 6.11 μmol, 66.2% yield). $^1$H NMR (500 MHz, DMSO-d$_6$) δ 7.82 (t, J=5.3 Hz, 1H), 7.27-7.21 (m, 2H), 6.96 (d, J=8.5 Hz, 1H), 6.92-6.86 (m, 2H), 5.83 (s, 1H), 4.40 (t, J=11.6 Hz, 1H), 4.29 (t, J=5.6 Hz, 2H), 4.06-3.94 (m, 2H), 3.84-3.70 (m, 4H), 2.69 (d, J=11.3 Hz, 1H), 2.58 (s, 3H), 1.97 (d, J=13.4 Hz, 1H), 1.84-1.62 (m, 6H), 1.62-1.52 (m, 3H), 1.22 (s, 3H), 1.18 (s, 9H). LCMS (M+H)=622.6.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

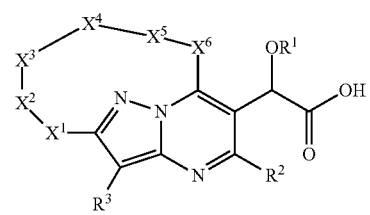

where:
R$^1$ is hydrogen or alkyl;
R$^2$ is hydrogen or alkyl;
R$^3$ is hydrogen, alkyl or halo;
X$^1$ is —CONH—, —CONHCH$_2$CO—, —CONHCH$_2$C(OH)H—, or —NH—;
X$^2$ is absent or benzyl wherein the benzyl can be substituted with 0-3 substituents selected from halo, alkyl, haloalkyl, alkoxy, and haloalkoxy;
X$^3$ is O or absent when X$^2$ is absent;
X$^4$ is alkylene or alkenylene;
X$^5$ is O or absent; and
X$^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or X$^6$ is phenyl or oxazinyl and is substituted with 0-3 substituents selected from halo, alkyl, haloalkyl, alkoxy, and haloalkoxy;
or a pharmaceutically acceptable salt thereof.

2. A compound of claim 1 where R$^1$ is hydrogen or alkyl; R$^2$ is hydrogen or alkyl; R$^3$ is hydrogen, alkyl or halo; X$^1$ is —CONH— or —NH—; X$^2$ is absent or benzyl wherein the benzyl can be substituted with 0-3 substituents selected from halo, alkyl, haloalkyl, alkoxy, and haloalkoxy; X$^3$ is O or absent when X$^2$ is absent; X$^4$ is alkylene or alkenylene; X$^5$ is O or absent; and X$^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents; or X$^6$ is phenyl or oxazinyl and is substituted with 0-3 substituents selected from halo, alkyl, haloalkyl, alkoxy, and haloalkoxy; or a pharmaceutically acceptable salt thereof.

3. A compound of claim 1 where R$^1$ is alkyl; R$^2$ is alkyl; R$^3$ is hydrogen; X$^1$ is —CONH— or —NH—; X$^2$ is absent or benzyl wherein the benzyl can be substituted with 0-3 substituents selected from halo, alkyl, haloalkyl, alkoxy, and haloalkoxy; X$^3$ is O or absent when X$^2$ is absent; X$^4$ is alkylene or alkenylene; X$^5$ is O or absent; and X$^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents; or X$^6$ is phenyl or oxazinyl and is substituted with 0-3 substituents selected from halo, alkyl, haloalkyl, alkoxy, and haloalkoxy; or a pharmaceutically acceptable salt thereof.

4. A compound of claim 3 where R$^1$ is alkyl; R$^2$ is alkyl; R$^3$ is hydrogen; X$^1$ is —CONH— or —NH—; X$^2$ is absent or benzyl wherein the benzyl can be substituted with 0-1 halo substituents; X$^3$ is O or absent when X$^2$ is absent; X$^4$ is alkylene or alkenylene; X$^5$ is O or absent; and X$^6$ is piperidinyl substituted with 0-1 alkyl substituents; or X$^6$ is phenyl or oxazinyl substituted with 0-1 halo substituents; or a pharmaceutically acceptable salt thereof.

5. A compound of claim 1 where $R^1$ is alkyl, $R^2$ is alkyl, and $R^3$ is hydrogen.

6. A compound of claim 1 where $X^1$ is —CONH—.

7. A compound of claim 1 where $X^1$ is —CONHCH$_2$CO—, —CONHCH$_2$C(OH)H—, or —NH—.

8. A compound of claim 1 where $X^2$ is benzyl substituted with 0-3 substituents selected from halo, alkyl, haloalkyl, alkoxy, and haloalkoxy; and $X^3$ is O or absent.

9. A compound of claim 1 where $X^2$ and $X^3$ are absent.

10. A compound of claim 1 where $X^4$ is propylene, propenylene, butylene, butenylene, pentylene, pentenylene, hexylene, hexenylene, heptylene or hetenylene.

11. A compound of claim 1 selected from the group consisting of
- (2S)-2-(tert-Butoxy)-2-[(12Z)-18-fluoro-3-methyl-24-oxo-15-oxa-2,23,26,27-tetraazapentacyclo[23.2.1.0$^{5,27}$.0$^{6,11}$.0$^{16,21}$]octacosa-1(28),2,4,6,8,10,12,16(21),17,19,25-undecaen-4-yl]acetic acid;
- (2S)-2-(tert-Butoxy)-2-[(21E)-31-chloro-16-fluoro-4-methyl-10-oxo-19,27-dioxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,21,28,31-undecaen-3-yl]acetic acid;
- (2S)-2-(tert-Butoxy)-2-[(20Z)-31-chloro-16-fluoro-4-methyl-10-oxo-19,27-dioxa-5,7,8,11,24-pentaazahexacyclo[22.6.2.1$^{6,9}$.0$^{2,7}$.0$^{13,18}$.0$^{28,32}$]tritriaconta-1(30),2,4,6 (33),8,13(18),14,16,20,28,31-undecaen-3-yl]acetic acid;
- (2S)-2-(tert-Butoxy)-2-[(21E)-31-chloro-16-fluoro-4-methyl-10-oxo-19,27-dioxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,21,28,31-undecaen-3-yl]acetic acid;
- (2S)-2-(tert-Butoxy)-2-[(20Z)-31-chloro-16-fluoro-4-methyl-10-oxo-19,27-dioxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,20,28,31-undecaen-3-yl]acetic acid;
- (2S)-2-(tert-Butoxy)-2-{31-chloro-16-fluoro-4-methyl-10-oxo-19,27-dioxa-5,7,8,11,24-pentaazahexacyclo[22.6.2.1$^{6,9}$.0$^{2,7}$.0$^{13,18}$.0$^{28,32}$]tritriaconta-1(30),2,4,6 (33),8,13(18),14,16,28,31-decaen-3-yl}acetic acid;
- (2S)-2-(tert-Butoxy)-2-[31-chloro-4-methyl-10-oxo-27-oxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,21,28,31-undecaen-3-yl]acetic acid;
- (2S)-2-(tert-Butoxy)-2-{31-chloro-4-methyl-10-oxo-27-oxa-5,7,8,11,24-pentaazahexacyclo[22.6.2.1$^{6,9}$.0$^{2,7}$.0$^{13,18}$.0$^{28,32}$]tritriaconta-1(30),2,4,6(33),8,13(18),14,16,28,31-decaen-3-yl}acetic acid;
- (2S)-2-(tert-Butoxy)-2-[(21E)-16-fluoro-4,25-dimethyl-10-oxo-19,24-dioxa-1,5,7,8,11-pentaazapentacyclo[22.6.2.1$^{6,9}$.0$^{2,7}$.0$^{13,18}$.0$^{28,32}$]triaconta-2,4,6(30),8,13,15,17,21-octaen-3-yl]acetic acid;
- (2S)-2-(tert-Butoxy)-2-{16-fluoro-4,25-dimethyl-10-oxo-19,24-dioxa-1,5,7,8,11-pentaazapentacyclo[23.2.2.1$^{6,9}$.0$^{2,7}$.0$^{13,18}$]triaconta-2,4,6(30),$_5$8,13 (18),14,16-heptaen-3-yl}acetic acid;
- (2S)-2-(tert-Butoxy)-2-[(21E)-4-methyl-10-oxo-19-oxa-1,5,7,8,11-pentaazapentacyclo[22.2.2.1$^{6,9}$.0$^{2,7}$.0$^{13,18}$]nonacosa-2,4,6(29),8,13 (18),14,16,21-octaen-3-yl]acetic acid;
- (2S)-2-(tert-Butoxy)-2-[(21Z)-4-methyl-10-oxo-19-oxa-1,5,7,8,11-pentaazapentacyclo[22.2.2.1$^{6,9}$.0$^{2,7}$.0$^{13,18}$]nonacosa-2,4,6(29),8,13(18),14,16,21-octaen-3-yl]acetic acid;
- (2S)-2-(tert-Butoxy)-2-{4-methyl-10-oxo-19-oxa-1,5,7,8,11-pentaazapentacyclo[22.2.2.1$^{6,9}$.0$^{2,7}$.0$^{13,18}$]nonacosa-2,4,6(29),8,13(18),14,16-heptaen-3-yl}acetic acid;
- (2S)-2-(tert-Butoxy)-2-[(21Z)-4-methyl-10-oxo-1,5,7,8,11-pentaazapentacyclo[22.2.2.1$^{6,9}$.0$^{2,7}$.0$^{13,18}$]nonacosa-2,4,6(29),8,13(18),14,16,21-octaen-3-yl]acetic acid;
- (2S)-2-(tert-Butoxy)-2-[(21E)-4-methyl-10-oxo-1,5,7,8,11-pentaazapentacyclo[22.2.2.1$^{6,9}$.0$^{2,7}$.0$^{13,18}$]nonacosa-2,4,6(29),8,13(18),14,16,21-octaen-3-yl]acetic acid
- (2S)-2-(tert-Butoxy)-2-[(21E)-16-fluoro-4-methyl-10-oxo-19-oxa-1,5,7,8,11-pentaazapentacyclo[22.2.2.1$^{6,9}$.0$^{2,7}$.0$^{13,18}$]nonacosa-2,4,6(29),8,13(18),14,16,21-octaen-3-yl]acetic acid;
- (2S)-2-(tert-Butoxy)-2-[(21Z)-16-fluoro-4-methyl-10-oxo-19-oxa-1,5,7,8,11-pentaazapentacyclo[22.2.2.1$^{6,9}$.0$^{2,7}$.0$^{13,18}$]nonacosa-2,4,6(29),8,13(18),14,16,21-octaen-3-yl]acetic acid;
- (2S)-2-(tert-Butoxy)-2-{16-fluoro-4-methyl-10-oxo-19-oxa-1,5,7,8,11-pentaazapentacyclo[22.2.2.1$^{6,9}$.0$^{2,7}$.0$^{13,18}$]nonacosa-2,4,6(29),8,13(18),14,16-heptaen-3-yl}acetic acid;
- (2S)-2-(tert-Butoxy)-2-[(15E)-4,19-dimethyl-18-oxa-1,5,7,8,10-pentaazatetracyclo[17.2.2.1$^{6,9}$.0$^{2,7}$]tetracosa-2,4,6(24),8,15-pentaen-3-yl]acetic acid;
- (2S)-2-(tert-Butoxy)-2-[(20E)-4,24-dimethyl-18,23-dioxa-1,5,7,8,10-pentaazapentacyclo[22.2.2.1$^{6,9}$.0$^{2,7}$.0$^{12,17}$]nonacosa-2,4,6(29),8,12(17),13,15,20-octaen-3-yl]acetic acid;
- (2S)-2-(tert-Butoxy)-2-{13-hydroxy-4,27-dimethyl-10-oxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetic acid;
- (2S)-2-(tert-Butoxy)-2-{13-hydroxy-4,27-dimethyl-10-oxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetic acid; and
- (2S)-2-(tert-Butoxy)-2-{4,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetic acid or a pharmaceutically acceptable salt thereof.

12. A composition useful for treating HIV infection comprising a therapeutic amount of a compound of claim 1 and a pharmaceutically acceptable carrier.

13. The composition of claim 12 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

14. A method for treating HIV infection comprising administering a therapeutically effective amount of a compound of claim 1, or a pharmaceutically acceptable salt thereof, to a patient in need thereof.

15. The method of claim 14 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

\* \* \* \* \*

UNITED STATES PATENT AND TRADEMARK OFFICE
CERTIFICATE OF CORRECTION

PATENT NO. : 9,540,393 B2  
APPLICATION NO. : 14/773028  
DATED : January 10, 2017  
INVENTOR(S) : B. Narasimhulu Naidu et al.

Page 1 of 1

It is certified that error appears in the above-identified patent and that said Letters Patent is hereby corrected as shown below:

In the Claims

In Claim 11, Column 57, Line 54:
The portion of the claim reading:
"$[22.6.2.1^{6,9}.0^{2,7}.0^{13,18}.0^{28,32}]$"

Should read:
--$[23.2.2.1^{6,9}.0^{2,7}.0^{13,18}]$--.

In Claim 11, Column 57, Line 58:
The portion of the claim reading:
"$(30)_5 8$"

Should read:
--$(30),8$--.

Signed and Sealed this
Ninth Day of May, 2017

Michelle K. Lee
*Director of the United States Patent and Trademark Office*